(12) United States Patent
Carrison et al.

(10) Patent No.: US 7,662,143 B2
(45) Date of Patent: Feb. 16, 2010

(54) APPARATUS AND METHOD FOR TREATING INTRAVASCULAR DISEASE

(75) Inventors: Harold Carrison, Pleasanton, CA (US); Robert M. Abrams, Los Gatos, CA (US); Jesse E. Casados, San Ramon, CA (US); Roger Farnholtz, Fremont, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 558 days.

(21) Appl. No.: 10/629,114

(22) Filed: Jul. 29, 2003

(65) Prior Publication Data

US 2005/0027247 A1    Feb. 3, 2005

(51) Int. Cl.
*A61M 31/00* (2006.01)
(52) U.S. Cl. .................................... 604/509
(58) Field of Classification Search .............. 604/96.01, 604/101.01–101.05, 915, 916, 102.01–102.03, 604/917, 919; 606/191–194
See application file for complete search history.

(56) References Cited

U.S. PATENT DOCUMENTS

| | | | |
|---|---|---|---|
| 4,423,725 A | | 1/1984 | Baran et al. |
| 4,573,966 A | * | 3/1986 | Weikl et al. ................. 604/509 |
| 4,655,746 A | | 4/1987 | Daniels et al. |
| 5,047,045 A | | 9/1991 | Arney et al. |
| 5,135,484 A | * | 8/1992 | Wright ......................... 604/28 |
| 5,156,594 A | | 10/1992 | Keith |
| 5,209,728 A | * | 5/1993 | Kraus et al. ............... 604/96.01 |
| 5,250,060 A | | 10/1993 | Carbo et al. |
| 5,328,471 A | * | 7/1994 | Slepian ................... 604/101.03 |

(Continued)

FOREIGN PATENT DOCUMENTS

DE    100 10 467    9/2001

(Continued)

OTHER PUBLICATIONS

U.S. Appl. No. 10/375,766 entitled "Composite Medical Device" filed Feb. 26, 2003.

(Continued)

*Primary Examiner*—Manuel A Mendez
(74) *Attorney, Agent, or Firm*—Crompton, Seager & Tufte LLC

(57) ABSTRACT

Medical devices and methods of treatment using medical devices, and more particularly, methods of treating a treatment site in a blood vessel and devices or apparatuses for use therewith. In some embodiments, a method and apparatus for treating a treatment site in a blood vessel using fluid movement or agitation adjacent the treatment site is disclosed. In some embodiments, an apparatus is provided including one or more deployable structures adapted to create fluid movement within the vessel. The apparatus is inserted into the vessel, and the deployable structure is positioned adjacent the treatment site. The deployable structure is used to create fluid movement adjacent to the treatment site. In some embodiments, a treatment material, such as a medicine or drug, is introduced into the vessel proximate the treatment site, and the deployable structure is used to create fluid movement or agitation adjacent the treatment site to create a better interface between the treatment site and the medicine, or to move the medicine into the treatment site. In some embodiments, the fluid movement created by the deployable member aids in removal of tissue or other material from the treatment site.

41 Claims, 20 Drawing Sheets

U.S. PATENT DOCUMENTS

| | | | |
|---|---|---|---|
| 5,370,657 A | 12/1994 | Irie | |
| 5,380,273 A | 1/1995 | Dubrul et al. | |
| 5,397,307 A * | 3/1995 | Goodin | 604/103.07 |
| 5,460,610 A | 10/1995 | Michael | |
| 5,462,529 A | 10/1995 | Simpson et al. | |
| 5,498,236 A | 3/1996 | Dubrul et al. | |
| 5,554,119 A * | 9/1996 | Harrison et al. | 604/103.01 |
| 5,626,605 A | 5/1997 | Irie et al. | |
| 5,702,439 A * | 12/1997 | Keith et al. | 604/96.01 |
| 5,709,704 A | 1/1998 | Nott et al. | |
| 5,713,848 A | 2/1998 | Dubrul et al. | |
| 5,772,674 A | 6/1998 | Nakhjavan | |
| 5,833,650 A | 11/1998 | Imran | |
| 5,893,869 A | 4/1999 | Barnhart et al. | |
| 5,925,016 A | 7/1999 | Chornenky et al. | |
| 6,022,336 A * | 2/2000 | Zadno-Azizi et al. | 604/101.05 |
| 6,027,520 A * | 2/2000 | Tsugita et al. | 606/200 |
| 6,051,014 A * | 4/2000 | Jang | 606/200 |
| 6,066,149 A | 5/2000 | Samson et al. | |
| 6,126,635 A | 10/2000 | Simpson et al. | |
| 6,165,200 A | 12/2000 | Tsugita et al. | |
| 6,171,327 B1 | 1/2001 | Daniel et al. | |
| 6,251,084 B1 | 6/2001 | Coelho | |
| 6,287,271 B1 | 9/2001 | Dubrul et al. | |
| 6,398,773 B1 * | 6/2002 | Bagaoisan et al. | 604/509 |
| 6,398,792 B1 * | 6/2002 | O'Connor | 606/128 |
| 6,450,988 B1 * | 9/2002 | Bradshaw | 604/96.01 |
| 6,454,741 B1 | 9/2002 | Muni et al. | |
| 6,454,775 B1 | 9/2002 | Demarais et al. | |
| 6,485,500 B1 * | 11/2002 | Kokish et al. | 606/194 |
| 6,508,782 B1 | 1/2003 | Evans et al. | |
| 6,537,294 B1 | 3/2003 | Boyle et al. | |
| 6,544,276 B1 | 4/2003 | Azizi | |
| 6,544,280 B1 | 4/2003 | Daniel et al. | |
| 6,547,754 B1 | 4/2003 | Evans et al. | |
| 6,572,605 B1 | 6/2003 | Humes | |
| 6,589,266 B2 | 7/2003 | Whitcher et al. | |
| 6,620,148 B1 * | 9/2003 | Tsugita | 604/509 |
| 6,623,452 B2 * | 9/2003 | Chien et al. | 604/103.01 |
| 6,663,589 B1 * | 12/2003 | Halevy | 604/96.01 |
| 2002/0022860 A1 | 2/2002 | Borillo et al. | |
| 2002/0062135 A1 | 5/2002 | Mazzocchi et al. | |
| 2003/0069520 A1 | 4/2003 | Skujins et al. | |
| 2003/0069521 A1 | 4/2003 | Reynolds et al. | |
| 2003/0078519 A1 | 4/2003 | Salahieh et al. | |

FOREIGN PATENT DOCUMENTS

| | | |
|---|---|---|
| WO | WO 96/04952 | 2/1996 |

OTHER PUBLICATIONS

U.S. Appl. No. 10/376,068 entitled "Elongated Intracorporal Medical Device" filed Feb. 26, 2003.

* cited by examiner

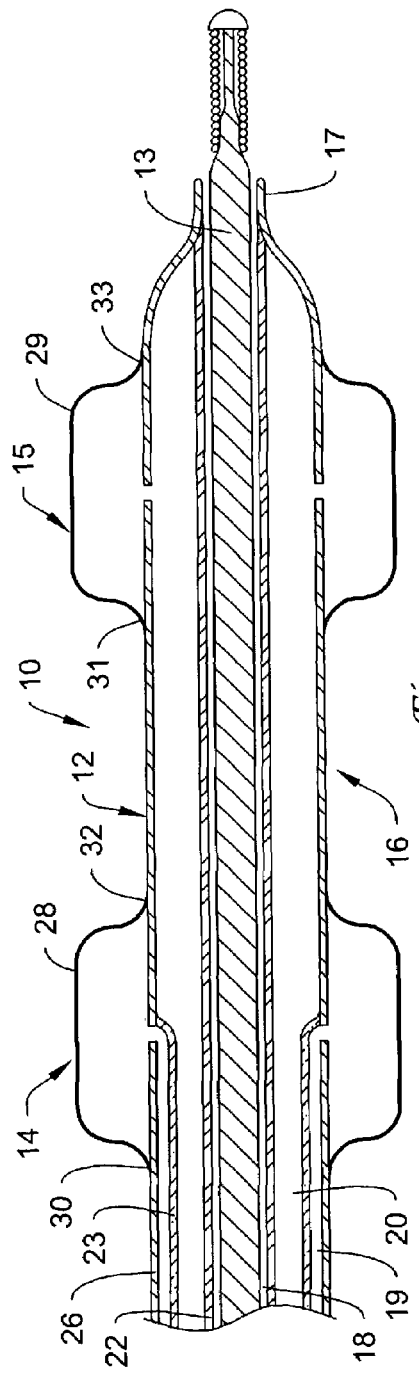
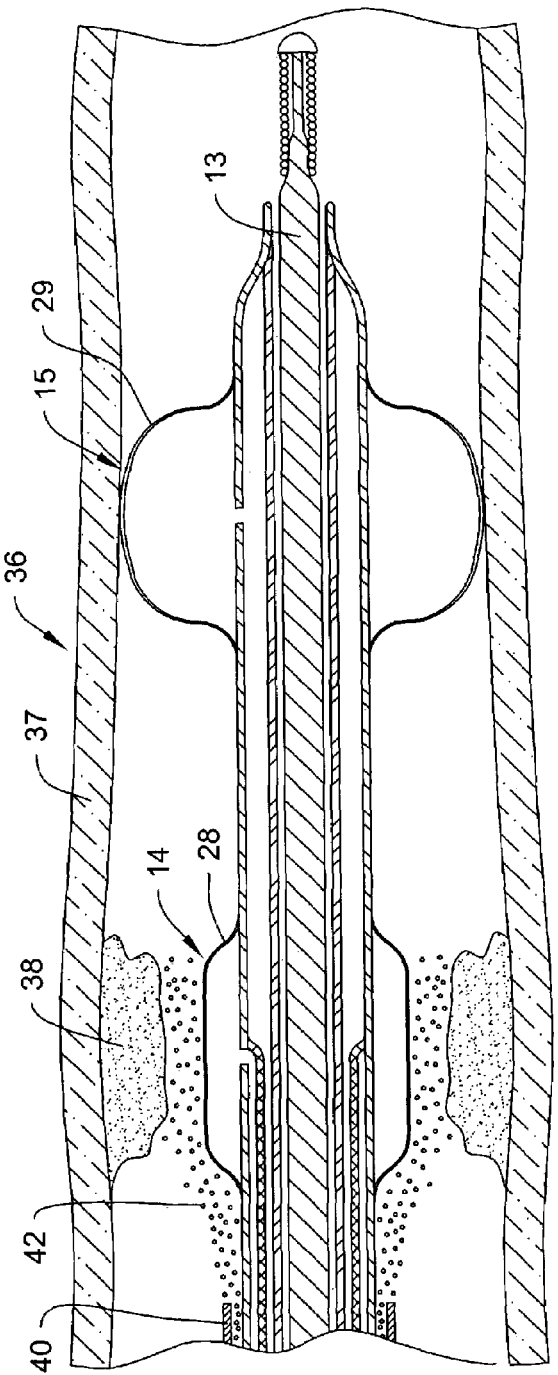

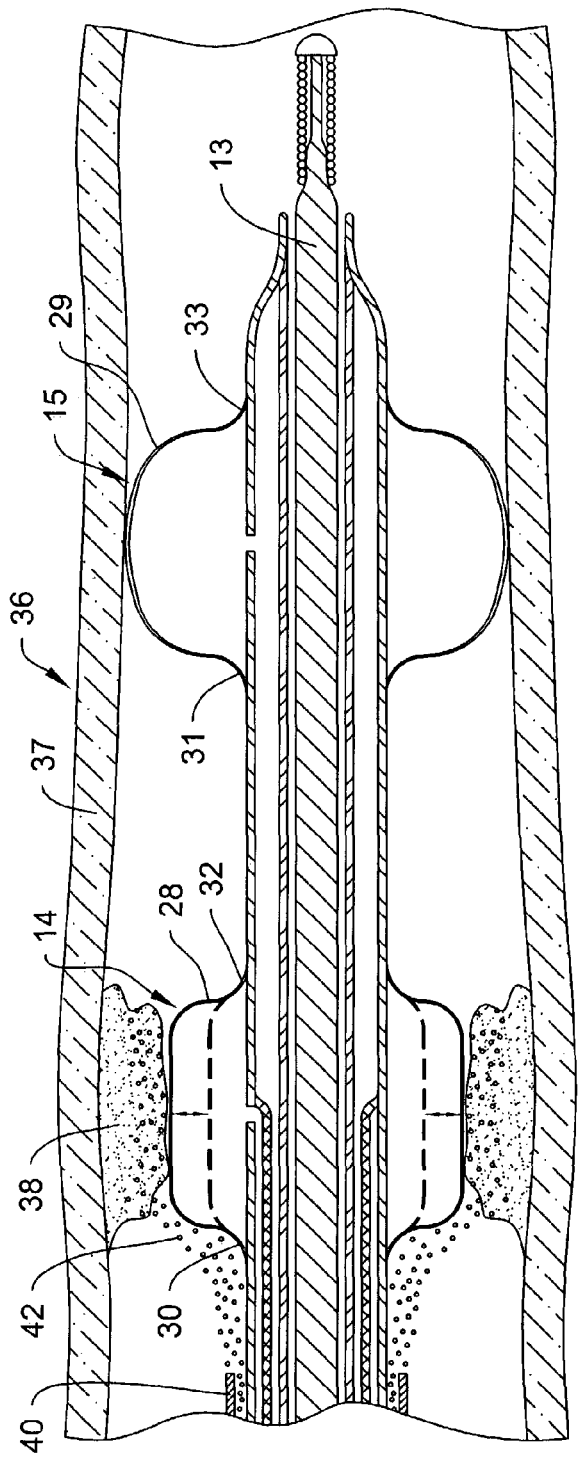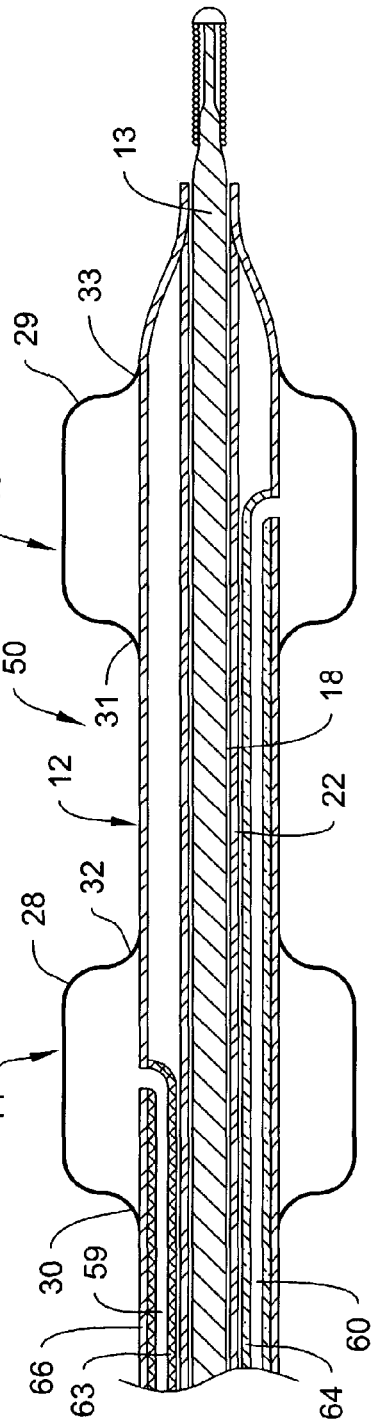
Fig. 3
Fig. 4

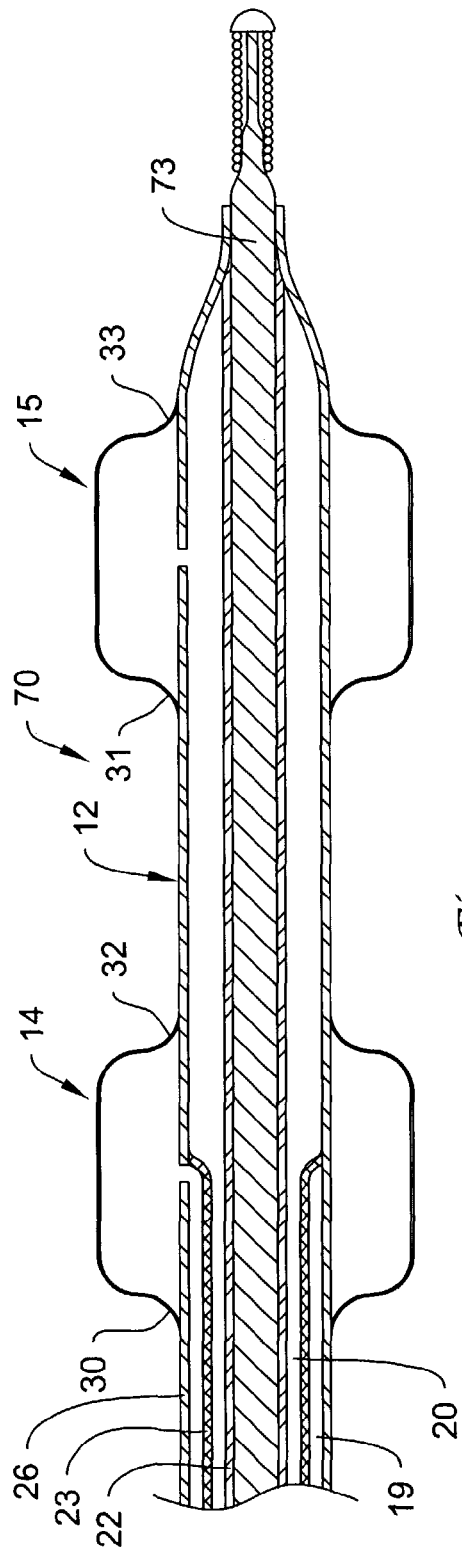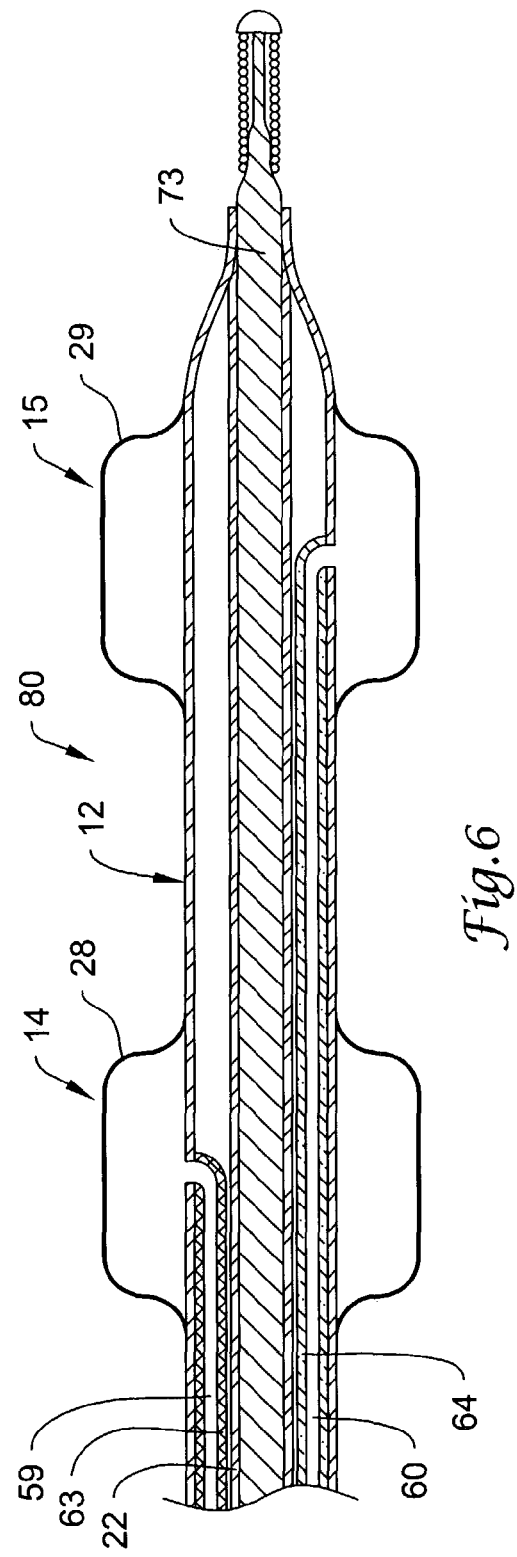

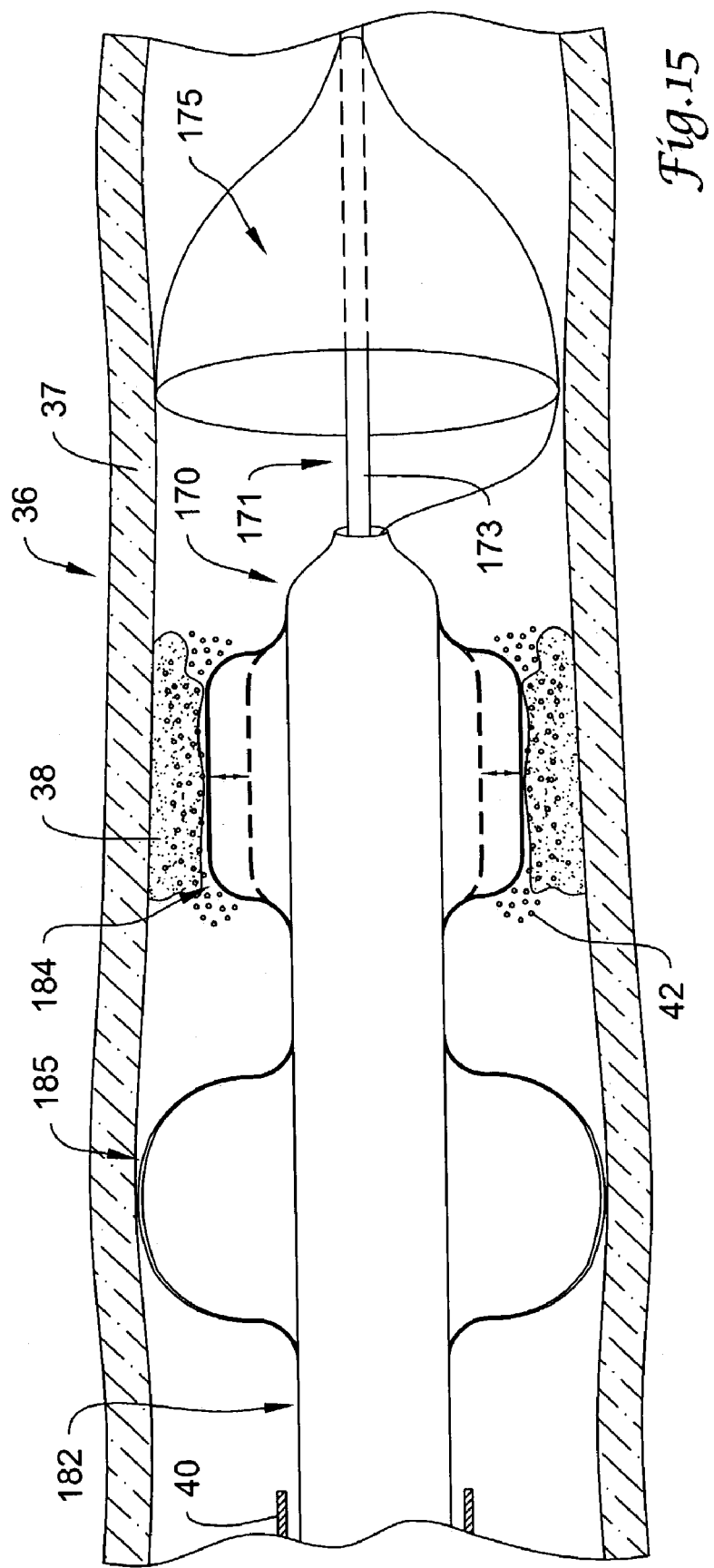

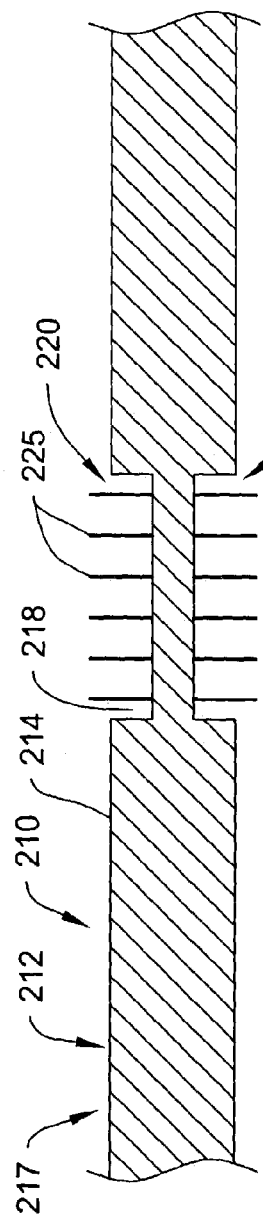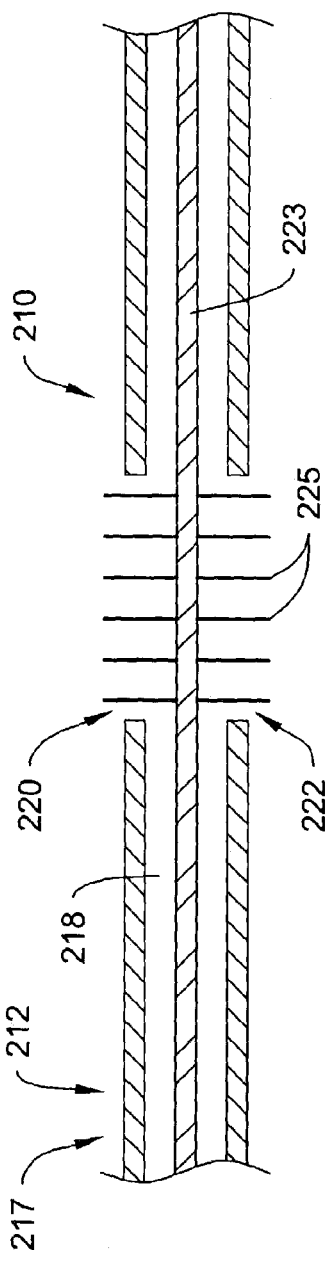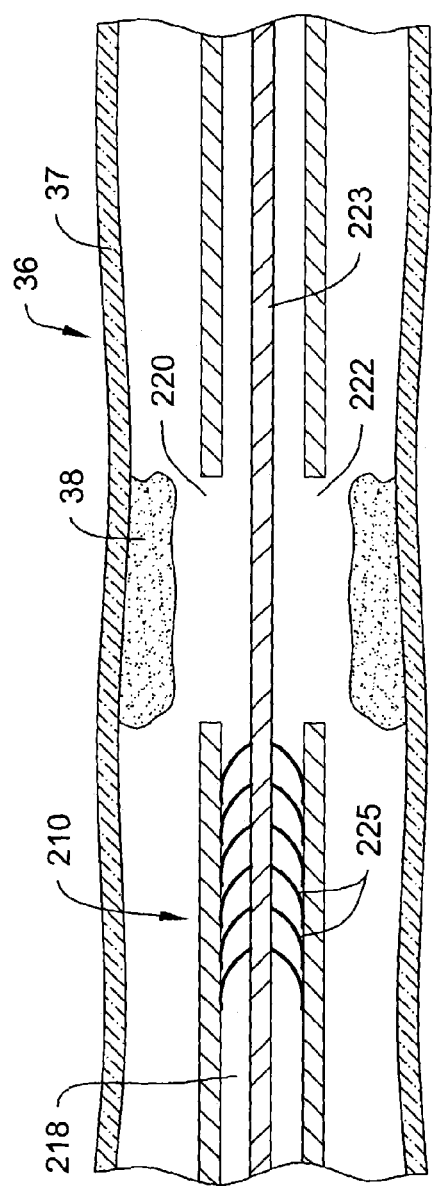

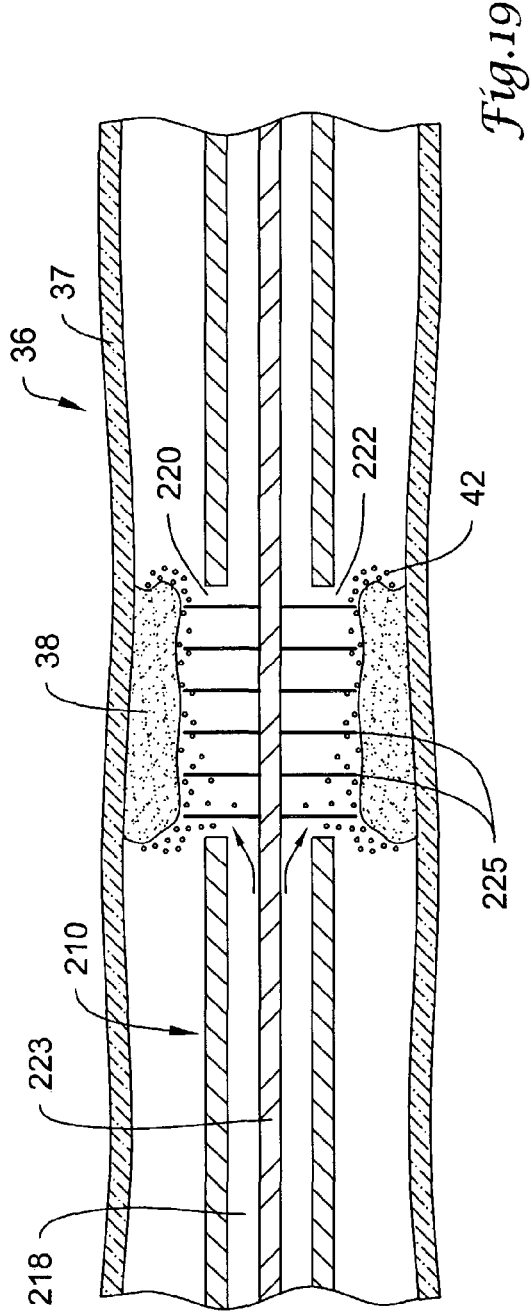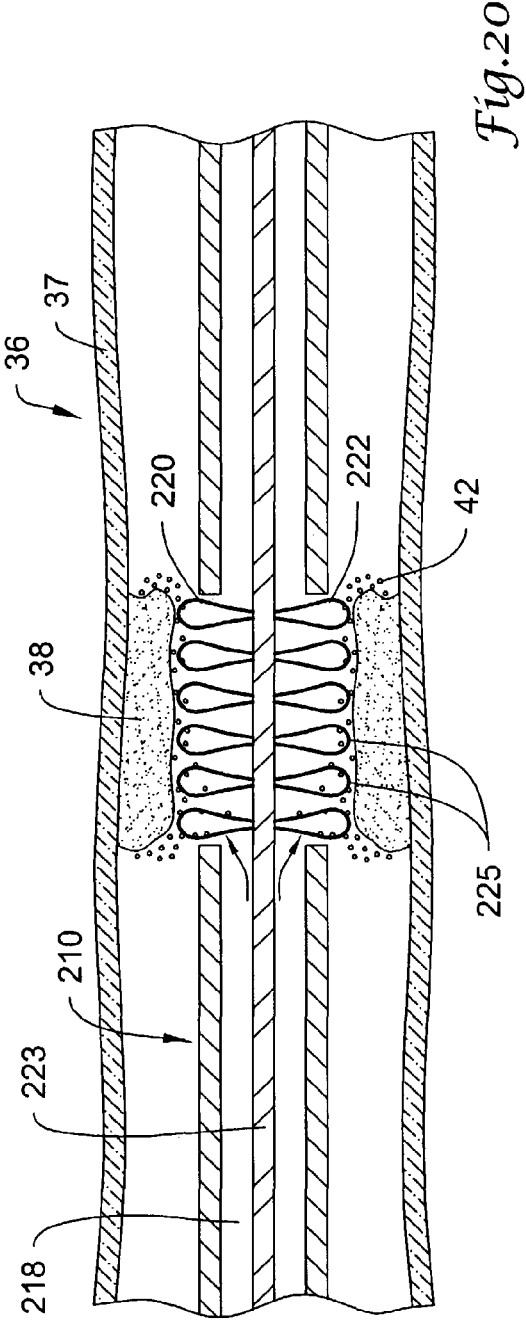

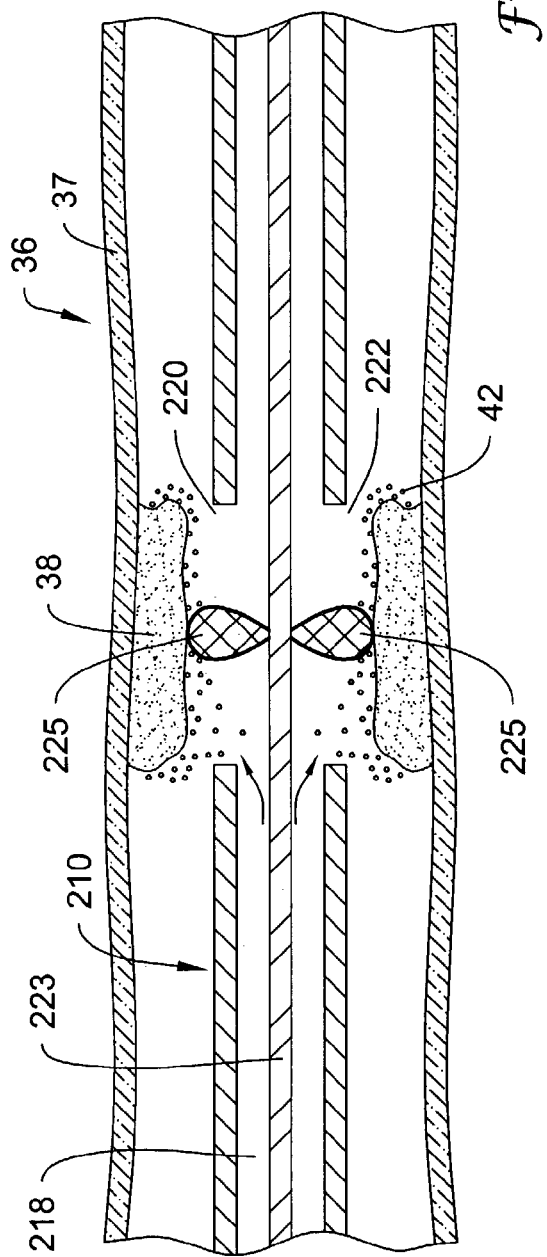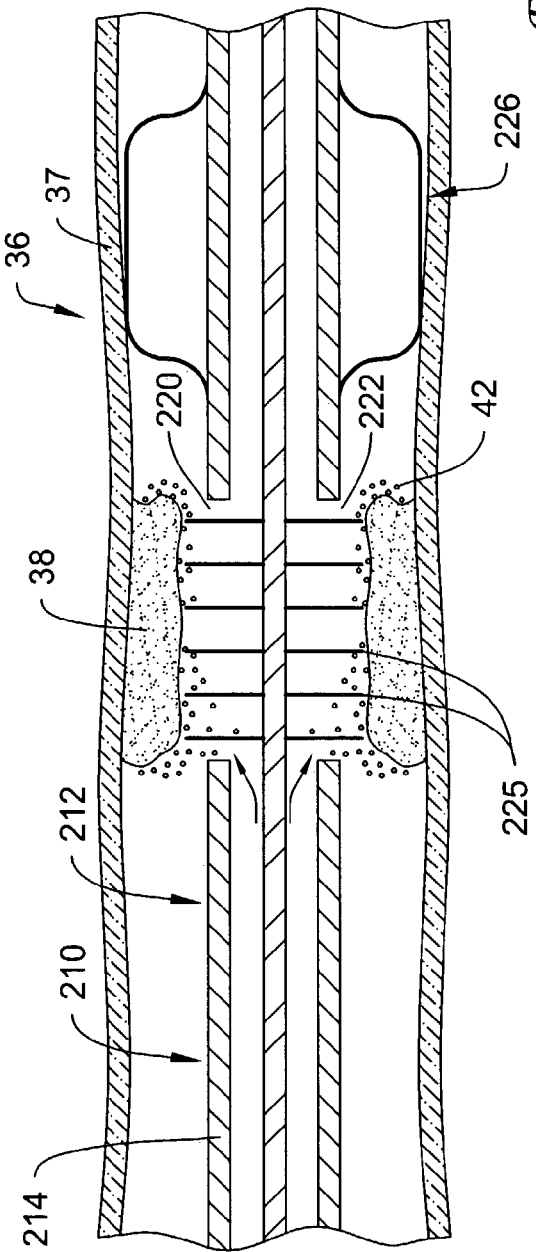

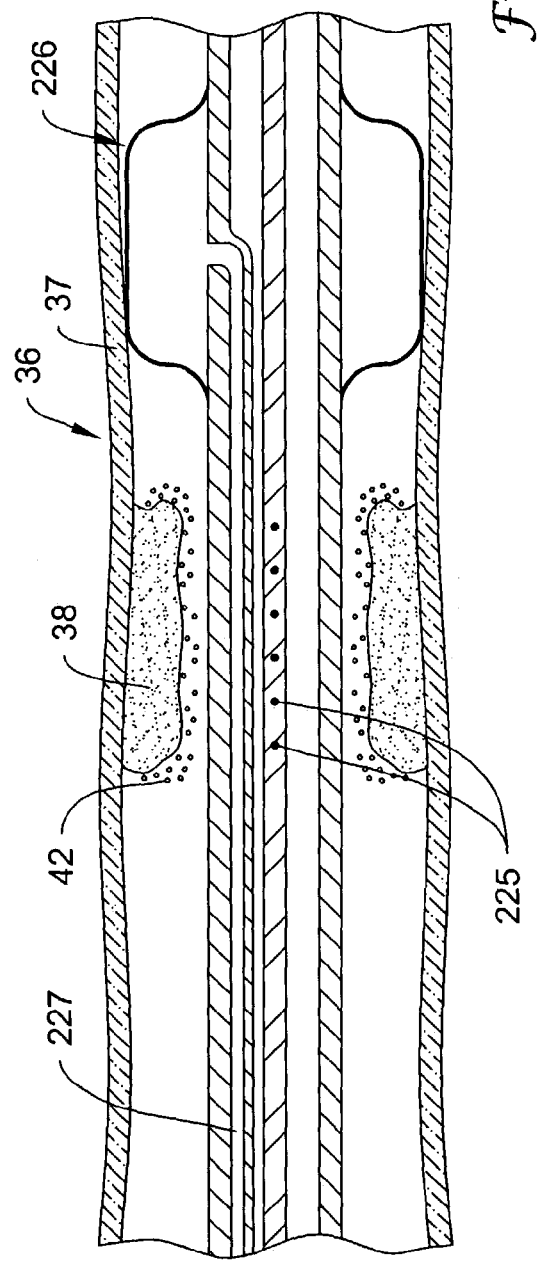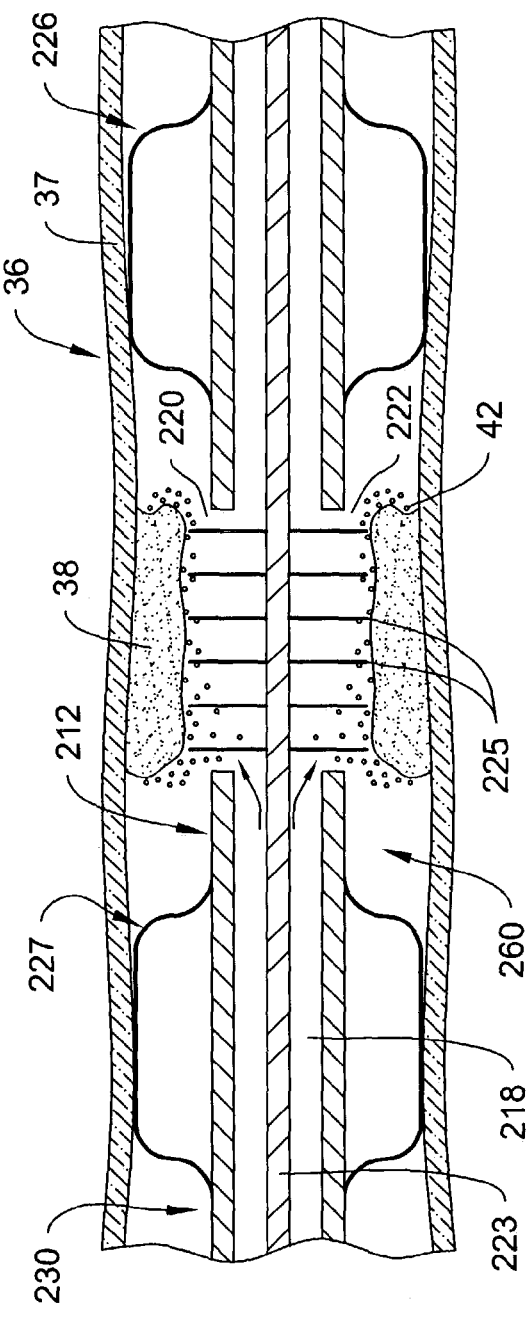

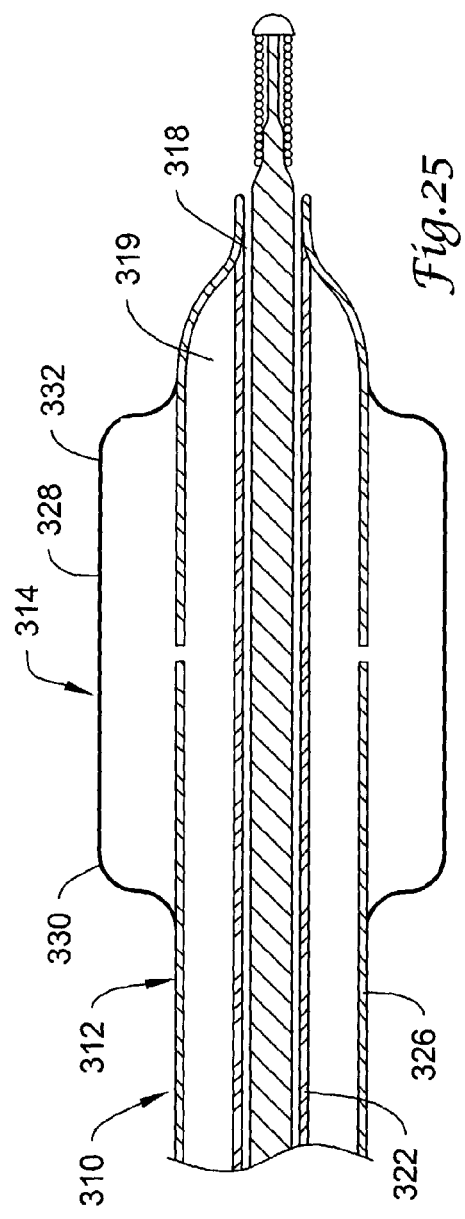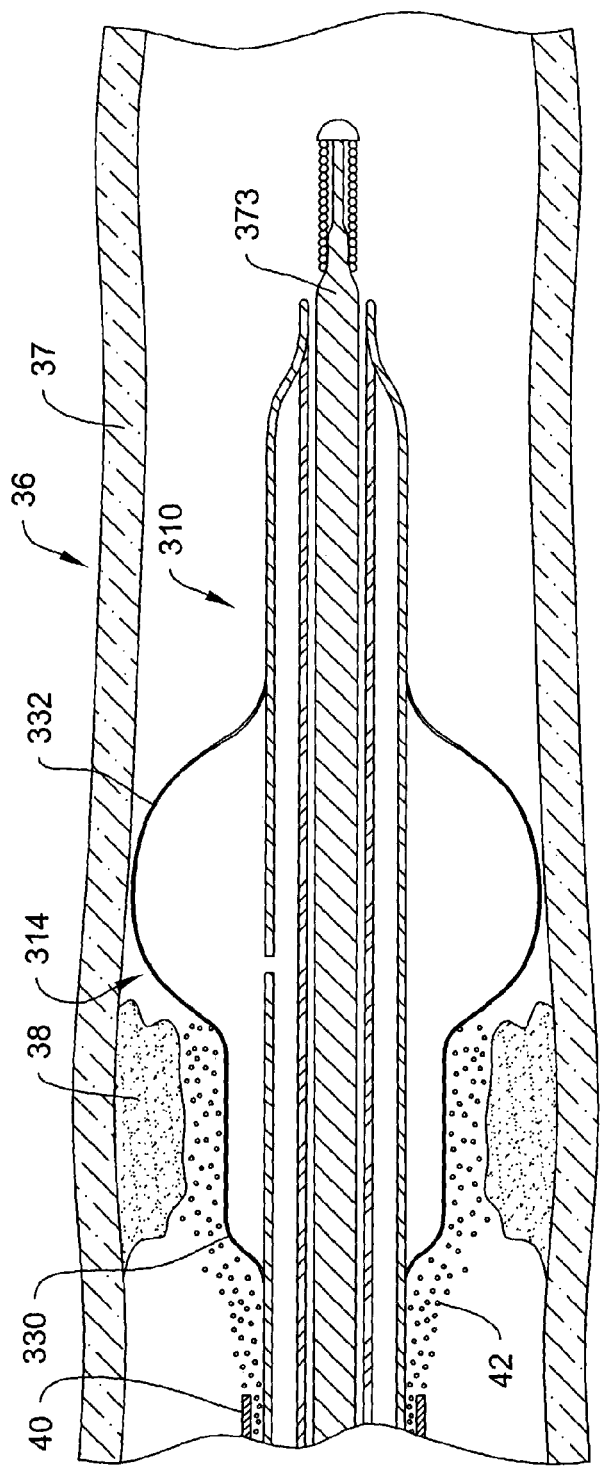

APPARATUS AND METHOD FOR TREATING INTRAVASCULAR DISEASE

FIELD OF THE INVENTION

The invention relates to the medical devices and methods of treatment using medical devices, and more particularly the invention relates to methods of treating a treatment site in a blood vessel and devices or apparatuses for use therewith.

BACKGROUND

Intravascular diseases or conditions are commonly treated by relatively non-invasive techniques. For example, vessels in the anatomy of a patient may be treated using structures such as guidewires, catheters, and the like that are navigated intravascularly to a treatment area or site. For example, in the coronary area, procedures such as percutaneous transluminal angioplasty (PTA) and percutaneous transluminal coronary angioplasty (PTCA). Similar treatments using such devices are also known for use in peripheral or cranial blood vessels. These therapeutic techniques are well known in the art and may involve the use of a balloon catheter with a guidewire, possibly in combination with other intravascular devices, such as stents. Some typical balloon catheters have an elongate shaft with a balloon attached proximate the distal end and a manifold attached to the proximal end. In use, some balloon catheters are advanced over a guidewire such that the balloon is positioned adjacent a treatment site in a diseased or occluded vessel. The balloon is then inflated and the restriction in the vessel is opened.

In some other cases, intravascular diseases can be treated with drugs. For example, in some such embodiments, medicine, such as a blood clot or stenosis dissolving drug, is introduced into the vessel. The drugs may act to dissolve the clot or stenosis.

A number of different catheter structures and assemblies, and method for use thereof, are known, each having certain advantages and disadvantages. Additionally, a number of different methods and devices adapted for using drugs to treat intravascular disease are known, each having certain advantages and disadvantages. However, there is an ongoing need to provide alternative structures and assemblies, and methods for treating intravascular disease.

SUMMARY

In some aspects, the invention relates to several alternative designs, materials, and methods of manufacturing alternative structures and assemblies, and alternative methods of treating intravascular disease.

For example, in some aspects, the invention relates to a method and apparatus for treating a treatment site in a blood vessel using fluid movement or agitation adjacent the treatment site. In some embodiments, an apparatus is provided including one or more deployable structures adapted to create fluid movement within the vessel. The apparatus is inserted into the vessel, and the deployable structure is positioned adjacent the treatment site. The deployable structure is used to create fluid movement adjacent to the treatment site. In some embodiments, a treatment material, such as a medicine or drug, is introduced into the vessel proximate the treatment site, and the deployable structure is used to create fluid movement or agitation adjacent the treatment site to create a better interface between the treatment site and the medicine, or to move the medicine into the treatment site. In some embodiments, the fluid movement created by the deployable member aids in removal of tissue or other material from the treatment site.

The above summary of some embodiments is not intended to describe each disclosed embodiment or every implementation of the present invention. The Figures, and Detailed Description which follow more particularly exemplify these embodiments.

BRIEF DESCRIPTION OF THE DRAWINGS

The invention may be more completely understood in consideration of the following detailed description of various embodiments of the invention in connection with the accompanying drawings, in which:

FIG. 1 is a partial cross-sectional view of an example embodiment of an apparatus for use in treatment of vascular disease, the apparatus including an over-the-wire balloon catheter having two balloon assemblies and having a coaxial arrangement of lumens;

FIG. 2 is a partial cross-sectional view of the embodiment of a balloon catheter of FIG. 1 disposed in a blood vessel proximate a treatment site, wherein the distal balloon assembly has been inflated and a treatment material, such as a drug or medicine, is being released from a delivery device;

FIG. 3 is a partial cross-sectional view similar to that of FIG. 2, showing the proximal balloon assembly being inflated and deflated proximate the treatment site to cause movement of the drug adjacent the treatment site;

FIG. 4 is a partial cross-sectional view of another example embodiment of an over-the-wire balloon catheter having two balloon assemblies and having a side-by-side arrangement of lumens;

FIG. 5 is a partial cross-sectional view of an example embodiment of a fixed-wire balloon catheter having two balloon assemblies and having a coaxial arrangement of lumens;

FIG. 6 is a partial cross-sectional view of another example embodiment of a fixed-wire balloon catheter having two balloon assemblies and having a side-by-side arrangement of lumens;

FIG. 15 is a partial side view of another example embodiment of balloon catheter similar to that shown in FIGS. 13-14, but including two balloon assemblies shown in cross-section, and showing the distal protection filter on the core member in a deployed state, a treatment material, such as a drug, within the vessel, the proximal balloon assembly in an inflated state, and the distal balloon assembly being inflated and deflated proximate the treatment site to cause movement of the drug adjacent the treatment site;

FIG. 16 is a partial side view of another example embodiment of an apparatus for use in treatment of vascular disease, the apparatus including a catheter having a tubular body having cutout portions, and showing filaments attached to a core member extending through the cutout portions;

FIG. 17 is a partial cross-sectional view of the catheter of FIG. 16, showing the core member and the filaments attached thereto;

FIG. 18 is a partial cross-sectional view of the catheter of FIGS. 16-17 disposed in a vessel proximate a treatment site, wherein the filaments on the core member are disposed within the lumen of the catheter proximal of the cutout areas;

FIG. 19 is a partial cross-sectional view of the catheter and vessel of FIG. 18, wherein the core member has been advanced such that the filaments are disposed within the cutout areas adjacent the treatment site, and a treatment material, such as a drug, is being released from the lumen of the catheter through the cutout areas and the filaments can be moved via the core wire to cause movement of the drug adjacent the treatment site and/or to remove portions of the treatment site;

FIG. 20 is a partial cross-sectional view of another example embodiment of an assembly for use in treatment of vascular disease similar to that shown in FIGS. 16-19, but wherein filaments attached to a core member are looped filaments, and FIG. 20 showing the core member has been advanced such that the filaments are disposed within the cutout areas adjacent the treatment site, and a treatment material, such as a drug, is being released from the lumen of the catheter through the cutout areas and the filaments can be moved via the core wire to cause movement of the drug adjacent the treatment site and/or to remove portions of the treatment site;

FIG. 21 is a partial cross-sectional view of another example embodiment of an assembly for use in treatment of vascular disease similar to that shown in FIGS. 16-20, but wherein impeller or paddle members are attached to a core member, and wherein the core member has been advanced such that the members are disposed within the cutout areas adjacent the treatment site, and a treatment material, such as a drug, is being released from the lumen of the catheter through the cutout areas and the members can be moved via the core wire to cause movement of the drug adjacent the treatment site and/or to remove portions of the treatment site;

FIG. 22 is a partial cross-sectional view of another example embodiment of an assembly for use in treatment of vascular disease similar to that shown in FIGS. 16-19, but wherein the catheter further includes a balloon assembly disposed thereon, and FIG. 22 showing the balloon member inflated in a position distal to the treatment site, the core member advanced such that the filaments are disposed within the cutout areas adjacent the treatment site, and a treatment material, such as a drug, being released from the lumen of the catheter through the cutout areas and wherein the filaments can be moved via the core wire to cause movement of the drug adjacent the treatment site and/or to remove portions of the treatment site;

FIG. 23 is a partial cross-sectional view of the assembly of FIG. 22, showing the cross-section when the assembly is rotated 90 degrees from that shown in FIG. 22, showing the inflation lumen for the balloon assembly;

FIG. 24 is a partial cross-sectional view of another example embodiment of an assembly for use in treatment of vascular disease similar to that shown in FIGS. 22-23, but wherein the catheter includes two balloon assemblies disposed thereon, and FIG. 24 showing the distal balloon assembly inflated in a position distal to the treatment site, the proximal balloon assembly inflated in a position proximal to the treatment site, the core member advanced such that the filaments are disposed within the cutout areas adjacent the treatment site, and a treatment material, such as a drug, being released from the lumen of the catheter through the cutout areas, wherein the filaments can be moved via the core wire to cause movement of the drug adjacent the treatment site and/or to remove portions of the treatment site;

FIG. 25 is a partial cross-sectional view of another example embodiment of an assembly for use in treatment of vascular disease, the assembly including an over-the-wire balloon catheter having a balloon assembly including a balloon member that is adapted to have sections of varying inflation pressures along the length thereof;

FIG. 26 is a partial cross-sectional view of the embodiment of a balloon catheter of FIG. 25 disposed in a blood vessel proximate a treatment site, wherein the distal portion of the balloon member has been inflated while the proximal portion remains deflated, and a treatment material, such as a drug, is being released from a delivery device;

Figure 7:
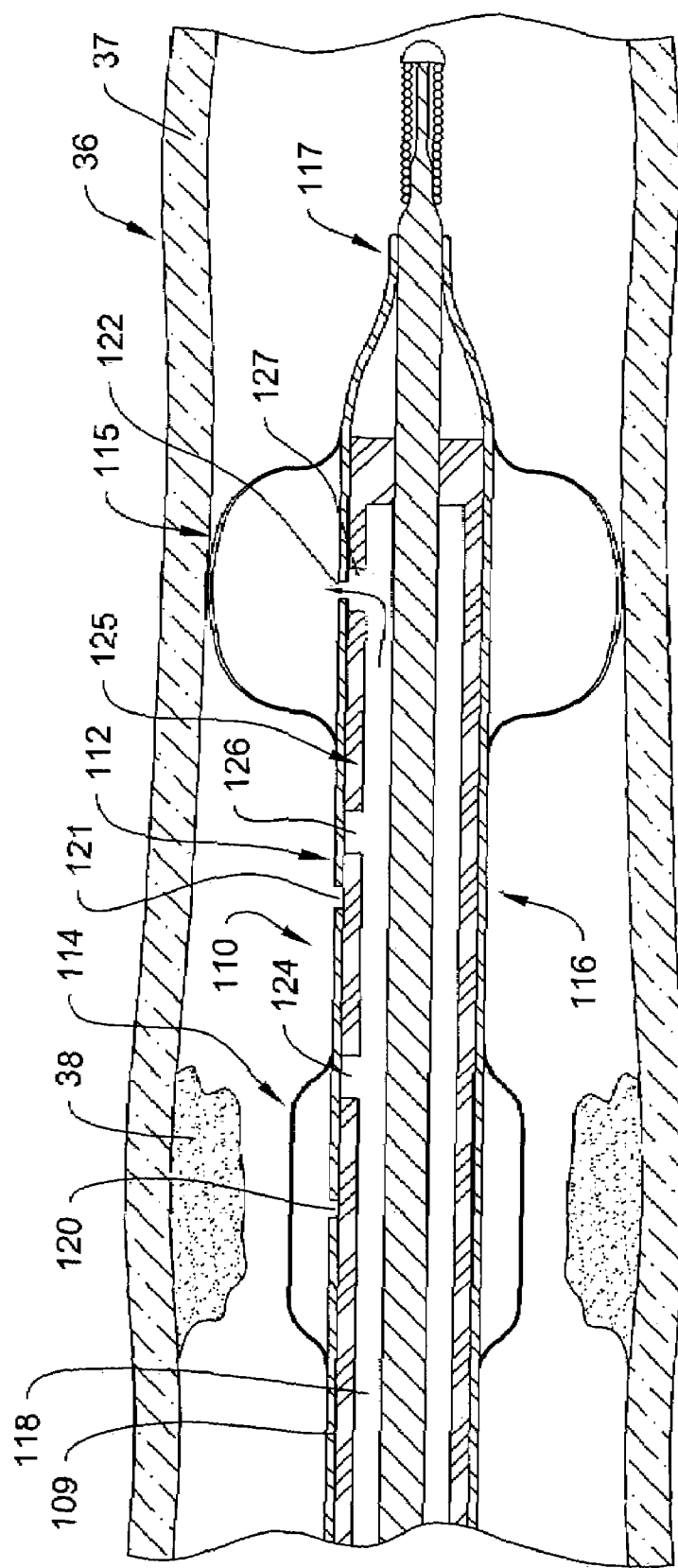
FIG. 7 is a partial cross-sectional view of another example embodiment of an assembly for use in treatment of vascular disease, the assembly including a balloon catheter having two balloon assemblies and a release port, and also including a selectively adjustable tubular member defining a lumen having multiple ports therein, the tubular member adapted for selective inflation/deflation of the balloon assemblies and for selective release of treatment materials through the release port, the catheter being disposed in a vessel proximate a treatment site and the distal balloon assembly being inflated.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION OF SOME EMBODIMENTS

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the resited value (i.e., having the same function or result). In many instances, the terms "about" may include numbers that are rounded to the nearest significant figure.

Weight percent, percent by weight, wt %, wt-%, % by weight, and the like are synonyms that refer to the concentration of a substance as the weight of that substance divided by the weight of the composition and multiplied by 100.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description of some embodiments should be read with reference to the drawings, wherein like reference numerals indicate like elements throughout the several views. The drawings, which are not necessarily to scale, depict some example embodiments and are not intended to limit the scope of the invention. Those skilled in the art and others will recognize that many of the examples provided have suitable alternatives which may also be utilized.

Referring now to the drawings, FIG. 1 is a cross-sectional view of one embodiment of an apparatus for use in treating intravascular disease including an over-the-wire (OTW) balloon catheter 10. Other intravascular structures or catheter embodiments are additionally suitable without deviating from the spirit and scope of the invention. For example, some other suitable intravascular catheters include fixed-wire (FW) catheters, single-operator-exchange (SOE) catheters, and the like, some examples discussed below. Some examples of OTW catheters are disclosed in commonly assigned U.S. Pat. No. 5,047,045 to Arney et al., which is incorporated herein by reference. Some examples of SOE balloon catheters are disclosed in commonly assigned U.S. Pat. No. 5,156,594 to Keith, which is incorporated herein by reference.

The balloon catheter 10 can include a shaft assembly 12, a first deployable balloon assembly 14, and a second deployable balloon assembly 15, each connected proximate the distal end of shaft assembly 12. In the embodiment shown, the first deployable balloon assembly 14 is disposed in a more proximal position on the shaft assembly 12 relative to the more distal position of the second deployable balloon assembly 15 on the shaft assembly 12. The shaft assembly 12 may have conventional dimensions and may be made of conventional materials suitable for intravascular navigation as in, for example, conventional navigation or treatment of blood clots, angioplasty or stent deployment procedures, and the like. The shaft assembly 12 includes a distal portion 16 and a distal end 17, and a proximal portion having a proximal end (not shown).

In some embodiments, the catheter shaft 12 comprises at least two or more lumens extending within the catheter shaft 12. The embodiment shown includes three lumens, including at least one guidewire lumen 18 and two inflation lumens 19 and 20. In some embodiments, the guidewire lumen 18 may extend the entire length of the catheter shaft 12 (e.g. over-the-wire catheter), or it may extend along a portion of the catheter shaft 12, wherein it exits the catheter shaft 12 in the distal portion proximate the distal end 17 (e.g. single operator exchange catheter). The first inflation lumen 19 allows fluid communication between an inflation source and the first deployable balloon assembly 14. The second inflation lumen 20 allows fluid communication between an inflation source and the second deployable balloon assembly 15. In general, the proximal ends of each of the inflation lumens 19 and 20 can be put into fluid communication with an inflation source while the distal end of the inflation lumens 19 and 20 are in fluid communication with the interior of the deployable balloon assemblies 14 and 15, respectively. The shaft assembly 12 may be a multiple lumen (i.e. side-by-side) design or a coaxial design as shown.

In the co-axial design shown, the shaft assembly 12 can include an inner tubular member 22, an intermediate tubular member 23, and an outer tubular member 26. The inner tubular member 22 defines the guidewire lumen 18, the intermediate tubular member 23 is co-axially disposed about the inner tubular member 22 to define the second annular inflation lumen 20 there between, and the outer tubular member 26 is co-axially disposed about the inner tubular member 22 and the intermediate tubular member 23 to define the first annular inflation lumen 19 there between.

In some embodiments, a manifold assembly (not shown) may be connected to the proximal end of the shaft assembly 12. Conventional OTW-type manifold assemblies are generally known, but other types of manifolds are contemplated. Such manifolds may include multiple branches, for example, one branch of a manifold assembly may connect an inflation source to the inflation lumen 19, and may be used to inflate and deflate (i.e. deploy and un-deploy) the expandable balloon 28 which the inflation lumen 19 is fluidly connected. Another branch of a manifold assembly may connect an inflation source to the inflation lumen 20, and may be used to inflate and deflate (i.e. deploy and un-deploy) the expandable balloon 29 which the inflation lumen 20 is fluidly connected. Another branch of a manifold assembly may connect to the guidewire lumen 18, and may be used for insertion of a guidewire 13 into the lumen 18.

The deployable balloon assemblies 14 and 15 can each include an expandable balloon portion 28 and 29, a proximal balloon waist 30 and 31, and a distal balloon waist 32 and 33, respectively. The proximal balloon waists 30 and 31 each connect the balloon assemblies 14 and 15, respectively, to the outer surface or the shaft assembly 12 using suitable attachment means, for example, an adhesive, a thermal bond, a mechanical bond, or the like. The distal balloon waists 32 and 33 similarly each connect the balloon assemblies 14 and 15, respectively, to the outer surface of the shaft assembly 12 using suitable attachment means, for example, an adhesive, a thermal bond, a mechanical bond, or the like. The shaft assembly 12 extends through at least a portion of the expandable balloon portions 28 and 29 in a generally coaxial manner. It should be understood that the embodiment shown is a schematic representation of one example embodiment, and that a broad variety of alternative structures and arrangements can be used to create the shaft assembly 12 and deployable balloon assemblies 14 and 15.

The size and the spacing of the balloon assemblies 14 and 15, can vary to a great extent, depending significantly upon the anatomy in which the catheter is being used, and the particular treatment site being treated. For example, the balloons can be designed to include a length and an expanded diameter that are particularly adapted for use in a desired anatomy or treatment site. Additionally, the spacing between balloon assemblies 14 and 15 along the length of the shaft assembly 12 can also be particularly designed for use in a desired anatomy or at a particular treatment site. For example, some catheters 10 and/or balloon assemblies 14 and 15 can be particularly adapted and/or configured for use within particular anatomies, such as the small vessels of the brain, in the peripheral vasculature, or in the coronary area, while other embodiments can be particularly adapted and/or configured for use in larger vessels in the anatomy. It should be understood, therefore, that the following dimensions are given by way of example only, and that any of a broad variety of dimensions either greater or smaller than those given are contemplated for use. In some embodiments, the balloon assemblies 14 and 15 can have a length in the range of about 0.5 to about 2.0 cm, and a diameter in an inflated or deployed state in the range of about 1.0 mm to about 10 mm. Additionally, in some embodiments, the balloon assemblies 14 and 15 can be spaced from each other along the length of the shaft assembly 12 by a distance in the range of about 0.5 to about 2.0 cm. The more distal balloon assembly (in this embodiment, balloon assembly 15) can be spaced from the distal tip of the shaft assembly 12 in the range of about 0.5 to about 2.0 cm.

It should be understood that in some embodiments, the distal and proximal balloon assemblies 14 and 15 may be different in size relative to one another. For example, each of the balloon assemblies 14 and 15 can have a size that is adapted and/or configured for operation in a particular vessel or region of a vessel. For example, if a vessel is tapered such that it is smaller in a distal region, the more distal balloon assembly may be smaller than the proximal balloon assembly.

Additionally, each of the balloon assemblies 14 and 15 can be essentially the same, or may be different. For example, one of the balloon assemblies may be adapted and/or configured for inflation to occlude the blood vessel, while the other of the balloon assemblies may be differently adapted and/or configured for repeated inflation/deflation to cause movement of fluid adjacent the treatment site. For example, one balloon assembly may include or be made of a less compliant or stiffer material that may be useful in occluding the vessel, while the other of the balloon assemblies may include or be made of a more complaint or flexible material that may be useful for repeated inflation/deflation.

A guidewire 13 is shown disposed within the guidewire lumen 18. The guidewire 13 may have conventional dimensions and may be made of conventional materials suitable for intravascular navigation as in, for example, conventional diagnostic, clot removal, angioplasty, stent deployment, or other such navigation and/or treatment procedures. Some examples of suitable guidewire are described in U.S. patent application Ser. Nos. 10/376,068 entitled "ELONGATED INTRACORPORAL MEDICAL DEVICE" filed on Feb. 26, 2003; 09/972,276 entitled "GUIDEWIRE WITH STIFFNESS BLENDING CONNECTION" filed on Oct. 5, 2001; 10/086,992 entitled "COMPOSITE GUIDEWIRE" filed on Feb. 28, 2002; and 10/375,766 entitled "COMPOSITE MEDICAL DEVICE" filed on Feb. 26, 2003, which are incorporated herein by reference.

Refer now to FIGS. 2-3 for a discussion of one example method of use of the balloon catheter described above with reference to FIG. 1. FIG. 2 shows the catheter 10 disposed in a blood vessel 36 having a vessel wall 37 and a treatment site 38. The treatment site 38 may be, for example, a blood clot, a stenosis, or other type of tissue, occlusion, or treatment area disposed in the blood vessel, or may be an opening to one or more branch vessels extending off of the vessel 36. For example, in some embodiments, the vessel may be a cranial vessel, and the treatment site may include a blood clot to be treated and/or removed. The catheter can be introduced and navigated within the vessel using convention techniques. For example, a guidewire 13 may be introduced into the vessel and navigated such that the distal portion thereof is advanced distally of the treatment site 38. The catheter 10 can then be advanced over the guidewire 13 into a position adjacent the treatment site 38. Alternatively, a guide member, such as a guide or introducer catheter 40 can be advanced to a position proximal of the treatment site, either alone or over a guidewire 13. The catheter 10 could then be advanced within the guide member 40 to a position adjacent the treatment site. In yet other embodiments, the catheter 10 could be introduced over a guidewire 13, and a guide or introducer member 40 could thereafter be introduced over the catheter 10. The guide or infusion member 40 could be used to introduce other devices, or treatment material, such as medicines or drugs. In the embodiment shown, both a guidewire 13 and a guiding or infusion catheter 40 are shown, but it should be understood that either or both need not necessarily be used.

The catheter 10 is advanced within the vessel 36 and disposed such that at least one of the balloon assemblies 14 or 15 is disposed adjacent the treatment site 38. In the embodiment shown, the more proximal balloon assembly 14 is disposed adjacent the treatment site 38, while the more distal balloon assembly 15 is disposed in a position distal to the treatment site 38. It should be understood that while the embodiment shown depicts the balloon assembly 14 in a position adjacent the treatment site such that it extends through or directly within the treatment site, in other embodiments, the balloon assembly may be positioned adjacent the treatment site more proximally or more distally of the treatment site than shown. For example, in some embodiments, the balloon assembly 14 may only partially overlap with the treatment site, or may even be spaced from the treatment site, but is still adjacent the treatment site. The more distal balloon assembly 15 can then be inflated to engage the inner surface of the vessel wall 37, and thereby occlude the flow of blood within the vessel. A treatment material 42, such as a drug or medicine, can be released into the vessel. In the embodiment shown, the treatment material 42 is released into the vessel adjacent the treatment site through the guiding or infusion catheter 40, however, in other embodiments, other modes of introducing or releasing the treatment fluid into the vessel are contemplated.

Refer now to FIG. 3, wherein the more proximal balloon assembly 14 is being inflated (deployed) and deflated (undeployed) repeatedly adjacent the treatment site 38. Such movement of the proximal balloon assembly 14 causes fluid movement within the vessel, and causes the treatment material 42 to make contact with the treatment site 38. It is believed that the movement or agitation caused by the repeated inflation/deflation of the proximal balloon assembly 14 can increase the amount of treatment material that makes contact with the treatment site. In some embodiments, it is also believed that the repeated inflation/deflation motion can force drugs into the treatment site. In any case, it is believed that the movement or agitation of the fluid, including the treatment material, adjacent the treatment site creates a better interface between the treatment material and the treatment site such that the treatment material can be more effective and act more quickly.

As indicated above, it is also contemplated that the treatment site may include or be disposed within a branch vessel, such as a branch artery or vein, the opening to which is disposed in the wall of the vessel 36. It may be desirable to create movement of the treatment material into the branch vessel. As such, the movement or agitation caused by the repeated inflation/deflation of the proximal balloon assembly 14 can increase the amount of treatment material that flows into the branch vessel.

Additionally, in this embodiment, the occlusion of the blood flow by the distal balloon 15 assembly can aid in maintaining the concentration of the treatment material in the vessel adjacent the treatment site. Normally, if a drug is released into a blood vessel, the drug will be diluted by, and carried away by the blood flowing in the vessel. However, in the embodiment shown, the occlusion of the blood flow by the distal balloon assembly 15 reduces the likelihood that the treatment material will quickly flow downstream within the vessel, and away from the treatment site. As such, the concentration of the treatment material adjacent the treatment site can be maintained at relatively high levels, and the treatment material can be maintained adjacent the treatment site in higher concentration levels for longer periods of time. By increasing the concentration of the treatment materials adjacent the treatment site, the effectiveness of the treatment material upon the treatment site can be enhanced. In embodiments where the treatment site may include or be disposed within a branch vessel, the occlusion of the blood flow by the distal balloon 15 assembly allows the treatment material to flow into the branch vessel in a more concentrated form.

It should also be understood that in other embodiments, the more distal balloon assembly 15 may be positioned within the vessel such that it is disposed adjacent the treatment site 38, while the more proximal balloon assembly 15 is disposed in a position proximal to the treatment site 38. The more proximal balloon assembly 15 could then be inflated to engage the inner surface of the vessel wall 37, and thereby occlude the flow of blood within the vessel from the proximal direction. A treatment material 42, such as a drug or medicine, could be released into the vessel adjacent the treatment site, either before or after the inflation of the distal balloon assembly, depending upon the mode of treatment material delivery. For example, if a treatment material 42 is delivered into the vessel at a position proximal of the proximal balloon assembly 15, for example through a guide or infusion catheter 40, the treatment material would be delivered first and at least a portion of it would be allowed to flow downstream, or distally, to a position distal of the proximal balloon assembly 15, and the proximal balloon assembly 15 would thereafter be inflated to occlude the flow of blood within the vessel.

In other embodiments, an alternative mechanism of delivery of the treatment material can be used such that the proximal balloon assembly 15 can be inflated first to occlude the flow of blood within the vessel, and the treatment material could be delivered to a point distal of the proximal balloon assembly 15 after inflation. For example, a treatment material delivery port and/or lumen could be defined in the shaft assembly 12 to deliver treatment material at a point distal of the proximal balloon assembly 15, or other delivery device or mechanism could be used. In either case, once the treatment material is delivered, the distal balloon assembly 15 can then be inflated and deflated to cause movement of the fluid within the vessel, and such movement or agitation can cause the treatment material to have a better and/or faster effect, and/or to flow into the treatment site. Additionally, the occlusion of the blood flow by the proximal balloon assembly 14 would reduce the likelihood that the treatment material will quickly flow downstream within the vessel away from the treatment site. This is because as the blood flow is occluded from the proximal side of the treatment site, the downstream, or distal, flow of blood will be reduced. As such, the concentration of the treatment material adjacent the treatment site can be maintained at relatively high levels, which can enhance the effectiveness of the treatment material upon the treatment site.

The treatment material 42 can be any of a broad variety of medicines or drugs, and can include those adapted for use in treating the particular disease or ailment presented by the patient. For example, if the treatment site includes a blood clot, or the like, that is being treated, a suitable blood clot dissolving drug or the like can be used. Some examples of such drugs include urokinase, TpA, streptokinase, reteplase, anistreplase, or other suitable drugs, and the like. For another example, if the treatment site includes another type of stenosis, such as buildup of plaque or diseased tissue within the vessel, a drug or medicine suitable for treatment of such diseases or ailments may be used.

Refer now to FIG. 4, which is a cross-sectional view of another example embodiment of an over-the-wire balloon catheter 50 similar to that shown in FIG. 1, wherein like reference numbers indicate similar structure. In this embodiment, however, the lumens are arranged in a side by side (or multi-lumen) design, rather than a coaxial design. The catheter shaft 12 still includes a guidewire lumen 18, and the inflation lumens 59 and 60 are not disposed coaxially about the guidewire lumen 18, but are rather defined by separate tubular structures extending within the catheter shaft 12. The inner tubular member 22 defines the guidewire lumen 18, a first intermediate tubular member 63 defines a first inflation lumen 59, and a second intermediate tubular member 64 defines a second inflation lumen 60. The shaft 12 may also include an outer tubular member 66 disposed about the tubular members 22, 63 and 64.

The first inflation lumen 59 allows fluid communication between an inflation source and the first deployable balloon assembly 14. The second inflation lumen 60 allows fluid communication between an inflation source and the second deployable balloon assembly 15. In general, the proximal ends of each of the inflation lumens 59 and 60 can be put into fluid communication with an inflation source while the distal end of the inflation lumens 59 and 60 are in fluid communication with the interior of the deployable balloon assemblies 14 and 15, respectively. As discussed above with regard to the first embodiment, in some embodiments, a manifold assembly (not shown) may be connected to the proximal end of the shaft assembly 12, and the manifold can include structure to connect inflation sources to the inflation lumens 59 and 60, and structure for insertion of a guidewire 13 into the guidewire lumen 18.

A guidewire 13 is shown disposed within the guidewire lumen 18. The guidewire 13 may have conventional dimensions and may be made of conventional materials suitable for intravascular navigation, as indicated above with reference to the first embodiment. Again, in some embodiments, the guidewire lumen 18 may extend the entire length of the catheter shaft 12 (e.g. over-the-wire catheter), or it may extend along a portion of the catheter shaft 12, wherein it exits the catheter shaft 12 in the distal portion proximate the distal end 17 (e.g. single operator exchange catheter). It should be understood that the embodiment shown is a schematic representation of one example embodiment, and that a broad variety of alternative structures and arrangements can be used to create the shaft assembly 12 and deployable balloon assemblies 14 and 15.

The apparatus depicted in FIG. 4 can be used in a similar manner to the apparatus discussed above in FIG. 1-3. The catheter 50 can be inserted into the vessel adjacent a treatment site 38. One of the distal or proximal balloon assemblies 14 or 15 can be positioned adjacent the treatment site 38, while the other of the distal or proximal balloon assemblies 14 or 15 is disposed at a location either proximal or distal to the treatment site, and inflated to engage the vessel wall and occlude the blood flow. A treatment material 42 can be introduced into the vessel such that at least a portion of it is disposed adjacent the treatment site, and the balloon assembly (either 14 or 15) disposed adjacent the treatment site can be repeatedly inflated and deflated to cause movement of the fluid, and create an interface between the treatment site and the treatment material, as discussed above with regard to the first embodiment. Also, as discussed above, the occlusion of the blood flow, for example, by the balloon assembly disposed at a location either proximal or distal to the treatment site can aid in maintaining the concentration of the treatment material 42 in the vessel 36 adjacent the treatment site 38.

FIG. 5 is a cross sectional view of a catheter 70 similar to that shown in FIG. 1, wherein like reference numbers indicate similar structure. In this embodiment, however, the catheter 70 is a fixed-wire (FW) balloon catheter design rather than an OTW design. The catheter 70, similar to catheter 10, can include a shaft assembly 12, and a first and second deployable balloon assemblies 14 and 15 connected to the shaft assembly 12. Two inflation lumens 19 and 20 are disposed in a coaxial arrangement in the shaft and are defined by inner, intermediate, and outer tubular members 22, 23 and 26 respectively. The first and second inflation lumens 19 and 20 allow fluid communication between inflation sources and the first and second deployable balloon assemblies 14 and 15, respectively. In general, the proximal ends of each of the inflation lumens 19 and 20 can be put into fluid communication with an inflation source while the distal end of the inflation lumens 19 and 20 are in fluid communication with the interior of the deployable balloon assemblies 14 and 15, respectively. As discussed above with regard to the first embodiment, in some embodiments, a manifold assembly (not shown) may be connected to the proximal end of the shaft assembly 12, and the manifold can include structure to connect inflation sources to the inflation lumens 19 and 20.

However in this embodiment, the inner surface of the inner tubular member 22 is attached to a central core member or wire 73. As such, the catheter is fixed to the central core member or wire 73, and hence, is a fixed wire design. The shaft assembly 12 can be attached to the central core member or wire 73 using suitable attachment means, for example, an adhesive, a thermal bond, a mechanical bond, an extrusion process, or the like. The central core member or wire 73 may have conventional dimensions and may be made of conventional materials suitable for use in a fixed wire device, and suitable for intravascular navigation. In some embodiments, central core member or wire 73 may have similar characteristics to a typical guidewire, for example guidewire 13 as indicated above with reference to the first embodiment.

The apparatus depicted in FIG. 5 can also be used in a similar manner to the apparatus discussed above in FIG. 1-3. The catheter 70 can be inserted into the vessel adjacent a treatment site. One of the distal or proximal balloon assemblies 14 or 15 can be positioned adjacent the treatment site 38, while the other of the distal or proximal balloon assemblies 14 or 15 is disposed at a location either proximal or distal to the treatment site, and inflated to engage the vessel wall. A treatment material 42 can be introduced into the vessel such that at least a portion of it is disposed adjacent the treatment site, and the balloon assembly (either 14 or 15) disposed adjacent the treatment site can be repeatedly inflated and deflated to cause movement of the fluid, and create an interface between the treatment site and the treatment material, as discussed above with regard to the first embodiment. Also, as discussed above, the occlusion of the blood flow, for example, by the balloon assembly disposed at a location either proximal or distal to the treatment site can aid in maintaining the concentration of the treatment material in the vessel adjacent the treatment site.

FIG. 6 is a cross sectional view of a fixed wire catheter 80 similar to that shown in FIG. 5, but in this embodiment, the lumens are arranged in a side by side (or multi-lumen) design similar to that shown in FIG. 4. The catheter shaft 12 includes the inner tubular member 22 having an inner surface that is attached to a central core member or wire 73. As such, the catheter is fixed to the central core member or wire 73, and hence, is a fixed wire design. The shaft assembly 12 can be attached to the central core member or wire 73 using suitable attachment means, for example, an adhesive, a thermal bond, a mechanical bond, an extrusion process, or the like. The central core member or wire 73 may have conventional dimensions and may be made of conventional materials suitable for use in a fixed wire device, as discussed above.

The inflation lumens 59 and 60 are defined by separate tubular structures extending within the catheter shaft 12. The first intermediate tubular member 63 defines the first inflation lumen 59, and the second intermediate tubular member 64 defines the second inflation lumen 60. The shaft 12 may also include an outer tubular member 66 disposed about the tubular members 22, 63 and 64.

The first and second inflation lumens 59 and 60 allow fluid communication between inflation sources and the first and second deployable balloon assemblies 14 and 15 respectively. In general, the proximal ends of each of the inflation lumens 59 and 60 can be put into fluid communication with an inflation source while the distal end of the inflation lumens 59 and 60 are in fluid communication with the interior of the deployable balloon assemblies 14 and 15, respectively. As discussed above with regard to the first embodiment, in some embodiments, a manifold assembly (not shown) may be connected to the proximal end of the shaft assembly 12, and the manifold can include structure to connect inflation sources to the inflation lumens 59 and 60.

The apparatus depicted in FIG. 6 can also be used in a similar manner to the apparatus discussed above in FIG. 1-3.

The catheter 80 can be inserted into the vessel adjacent a treatment site. One of the distal or proximal balloon assemblies 14 or 15 can be positioned adjacent the treatment site 38, while the other of the distal or proximal balloon assemblies 14 or 15 is disposed at a location either proximal or distal to the treatment site, and inflated to engage the vessel wall. A treatment material 42 can be introduced into the vessel such that at least a portion of it is disposed adjacent the treatment site, and the balloon assembly (either 14 or 15) disposed adjacent the treatment site can be repeatedly inflated and deflated to cause movement of the fluid, and create an interface between the treatment site and the treatment material, as discussed above with regard to the first embodiment. Also, as discussed above, the occlusion of the blood flow, for example, by the balloon assembly disposed at a location either proximal or distal to the treatment site can aid in maintaining the concentration of the treatment material in the vessel adjacent the treatment site.

Figure 8:
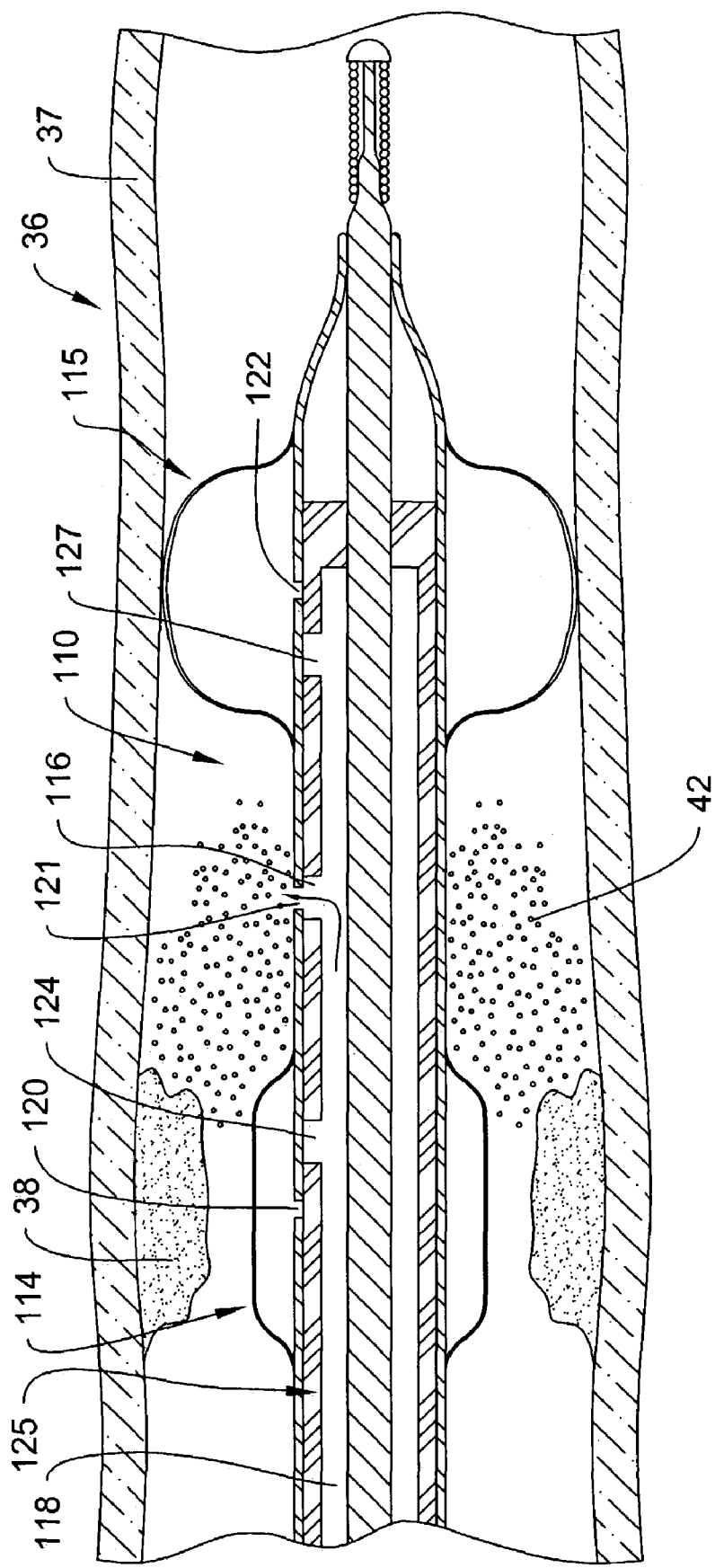
FIG. 8 is a partial cross-sectional view of the catheter and vessel of FIG. 7 showing a treatment material, such as a drug, being released through the release port.
Figure 9:
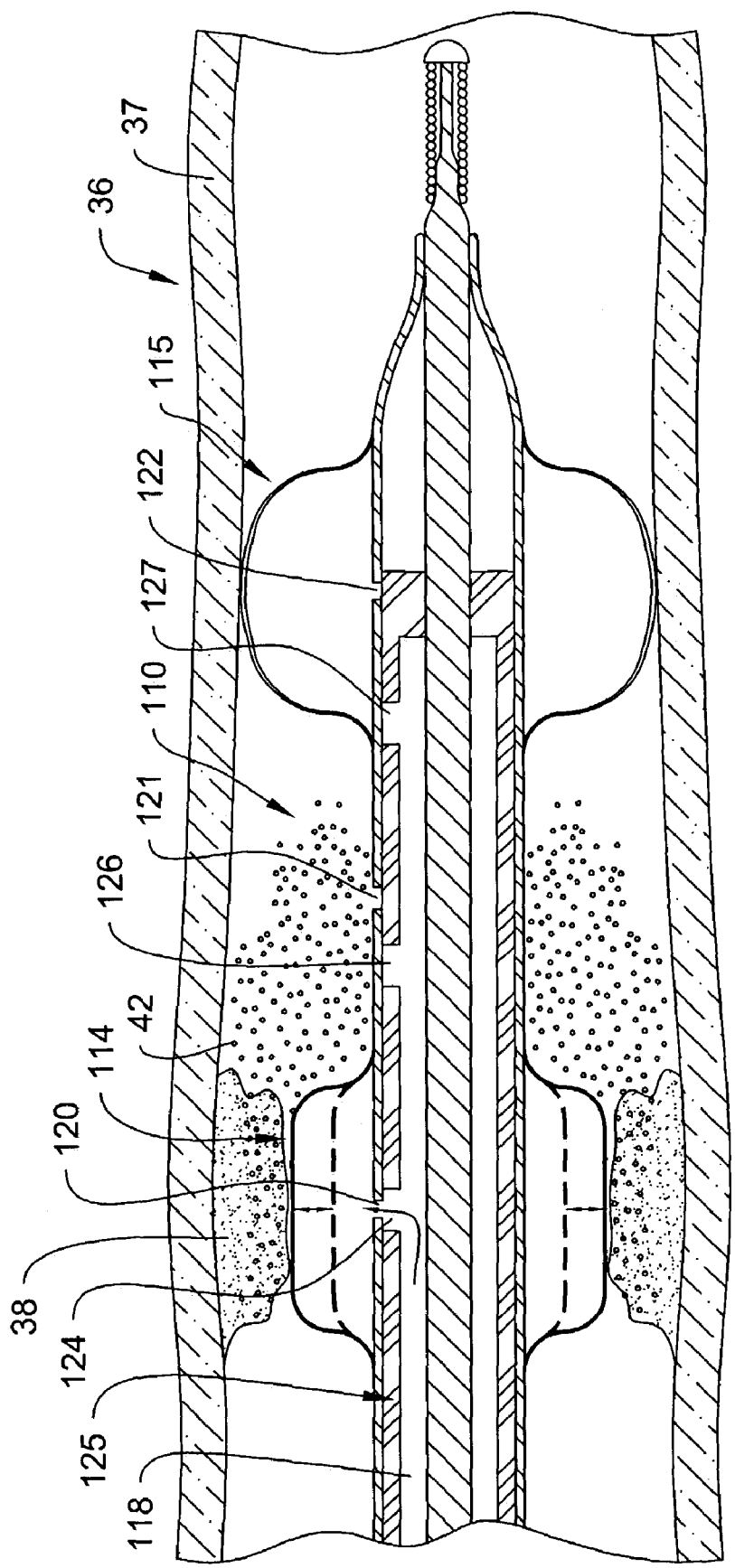
FIG. 9 is a partial cross-sectional view of the catheter and vessel of FIG. 8 showing the proximal balloon assembly being inflated and deflated proximate the treatment site to cause movement of the treatment material adjacent the treatment site.

FIGS. 7-9 show cross-sectional views of another alternative embodiment of an apparatus for use in treating intravascular disease, the apparatus including a balloon catheter 110. Although the catheter 110 is shown as a Fixed-Wire (FW) design, it should be understood that other catheter designs, for example, an OTW catheter design may be used without deviating from the spirit and scope of the invention.

Referring now to FIG. 7, the balloon catheter 110 can include a shaft assembly 112, a first deployable balloon assembly 114, and a second deployable balloon assembly 115, each connected proximate the distal end of shaft assembly 112 in a suitable manner, as discussed above. In the embodiment shown, the first deployable balloon assembly 114 is disposed in a more proximal position on the shaft assembly 112 relative to the more distal position of the second deployable balloon assembly 115 on the shaft assembly 112. The shaft assembly 112 may have conventional dimensions and may be made of conventional materials suitable for intravascular navigation as in, for example, conventional clot treatment, angioplasty or stent deployment procedures, and the like. The shaft assembly 112 includes a distal portion 116 and a distal end 117, and a proximal portion having a proximal end (not shown).

The shaft assembly 112 includes an outer tubular member 109 defining at least one lumen 118 extending within the catheter shaft 112. Other embodiments may include one or more additional lumens. The outer tubular member 109 of the catheter shaft 112 includes one or more opening disposed therein extending from the lumen 118 to the outer surface of the outer tubular member 109. In the embodiment shown, a first opening 120 is disposed under and is in fluid communication with the first balloon assembly 114. A second opening 121 is disposed in the outer tubular member 109 and is in fluid communication with the exterior of the catheter 110. In the embodiment shown, the second opening 121 is located between the first and second balloon assemblies 114 and 115, but it should be recognized that in other embodiments, the second opening 121 may be disposed at another location along the length of the catheter. For example, the second opening 121 may be disposed at a location proximal of the first balloon assembly 114, or at a location distal of the second balloon assembly 115. A third opening 122 is disposed under and is in fluid communication with the second balloon assembly 115.

The apparatus also includes a member 125 that is adapted to selectively block and/or allow fluid communication between the openings 120, 121, and 122, and the lumen 118. In this embodiment, the member 125 is a movable inner member 125 disposed within the lumen 118 that is adapted to slide within the lumen 118 along the longitudinal axis of the outer tubular member 109. The movable member 125 in this embodiment is a tubular member that includes a tubular wall including one or more openings defined in a distal portion thereof. For example, the embodiment shown includes a first, more proximal opening 124, a second, intermediate opening 126, and a third, more distal opening 127, each disposed in and extending through the wall of the member 125. The openings can be selectively spaced along the length of the member 125 such that when the member 125 is positioned at a predetermined location within the lumen 118, one or more of the openings 124, 126, or 127 can be selectively positioned adjacent to, and allow for fluid communication between the one or more of the openings 120, 121, or 122 and the lumen 118. Additionally, the openings 124, 126, or 127 can be selectively spaced along the length of the member 125 such that when the member 125 is positioned at an alternative predetermined location within the lumen 118, the openings 124, 126, or 127 can be selectively positioned away from one or more of the openings 120, 121, or 122, and as a result, the wall of the member 125 blocks fluid communication between the openings 120, 121, or 122 and the lumen 118. The tubular member 125 can extend the entire length of the shaft assembly 112, and can include a portion or structure that extends proximally from the shaft assembly 112 for manipulation by an operator. Additionally, the tubular member may also include a manifold assembly (not shown) connected to the proximal end thereof, for example a manifold assembly that may include structure to connect an inflation source in fluid communication with the lumen 118.

FIG. 7 shows the catheter 110 disposed in a blood vessel 36 having a vessel wall 37 and a treatment site 38. The treatment site 38 may be, for example, a blood clot, a stenosis, or other type of tissue, occlusion, or treatment area disposed in the blood vessel, or may be an opening to one or more branch vessels extending off of the vessel 36. The catheter 110 can be introduced and navigated within the vessel using convention techniques. During insertion and navigation of the catheter 110, the movable inner member 125 may be positioned within the lumen 118 such that none of the openings 124, 126 and 127 are positioned adjacent to the openings 120, 121, and 122 such that there is no fluid communication between the lumen 118 and the openings 120, 121, and 122. The catheter 110 is advanced within the vessel 36 and disposed such that at least one of the balloon assemblies 114 or 115 is disposed adjacent the treatment site 38. In the embodiment shown, the more proximal balloon assembly 114 is disposed adjacent the treatment site 38, while the more distal balloon assembly 115 is disposed in a position distal to the treatment site 38.

The movable inner member 125 can then be moved into a position within the lumen 118 such that the opening 126 is disposed adjacent to and in fluid communication with opening 122, and therefore allows for fluid communication between the lumen 118 and the balloon assembly 115. The openings 120 and 121 remain blocked by the inner member 125. The more distal balloon assembly 115 can then be inflated to engage the inner surface of the vessel wall 37 as shown in FIG. 7, and thereby occlude the flow of blood within the vessel.

Referring now to FIG. 8, the movable inner member 125 can also be moved into a position within the lumen 118 such that the openings 122 and 120 are blocked by the inner member 125. The blockage of opening 122 can maintain the balloon assembly 115 in an inflated or deployed configuration. The opening 126 is disposed adjacent to and in fluid communication with opening 121, and therefore allows for fluid communication between the lumen 118 and the exterior of the catheter 110. A treatment material 42, such as a drug or medicine, can be released into the vessel via the lumen 118 through the openings 126 and 121.

Referring now to FIG. 9, the movable inner member 125 can then be moved into a position within the lumen 118 such that the openings 121 and 122 are blocked by the inner member 125, but the opening 124 is disposed adjacent to and in fluid communication with opening 120, and therefore allows for fluid communication between the lumen 118 and the proximal balloon assembly 114. The balloon assembly 114 can then be inflated (deployed) and deflated (un-deployed) repeatedly adjacent the treatment site 38 to cause movement of the fluid, and create an interface between the treatment site 38 and the treatment material 42, as discussed above with regard to the first embodiment. Also as discussed above, the occlusion of the blood flow by the distal balloon assembly 115 can aid in maintaining the concentration of the treatment material in the vessel adjacent the treatment site.

Furthermore, it should be understood that in other embodiments, the more distal balloon assembly 115 may be positioned within the vessel such that it is disposed adjacent the treatment site 38 and can be used to create movement in the fluid, while the more proximal balloon assembly 114 is disposed in a position proximal to the treatment site 38 and could be used to occlude the vessel 36, the operation of the inner member 125 would essentially be reversed.

Additionally, it should be understood that in other embodiments the outer tubular member 114 and/or the inner member 125 can include more or fewer openings defined therein, depending somewhat upon the number of balloon assemblies and/or drug release ports desired, and upon the desired function of the device. For example, it is contemplated that the inner member 125 of the embodiment shown may include only one or two openings defined therein, and the inner member 125 could be adapted and/or configured such that one or two openings therein could selectively, and in at least some embodiments, separately, allow fluid communication between the openings in the outer tubular member 109 and the lumen 118 by appropriate positioning of the one or two openings.

Figure 10:
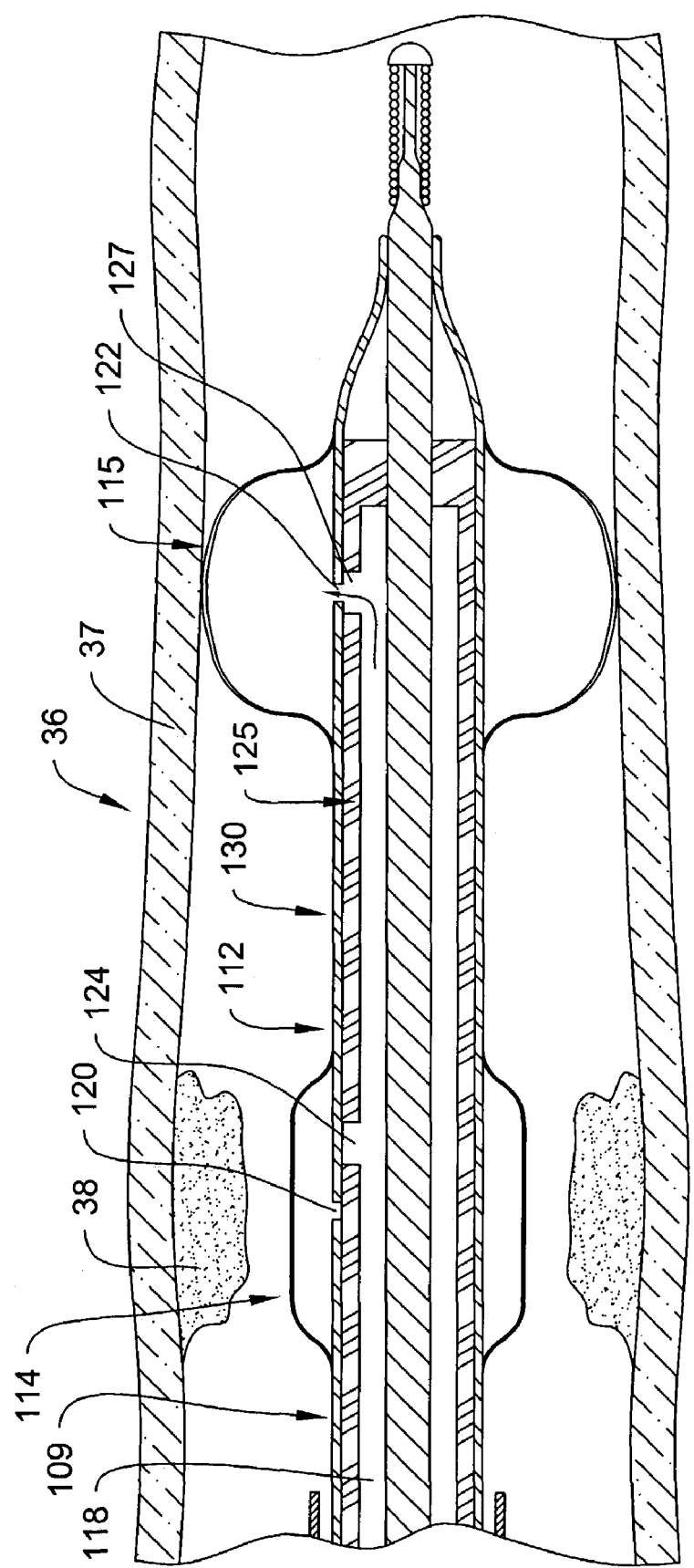
FIG. 10 is a partial cross-sectional view of another example embodiment of a balloon catheter similar to that shown in FIGS. 7-9, having two balloon assemblies, but not including a release port, the catheter being disposed in a vessel proximate a treatment site and the distal balloon assembly being inflated.
Figure 11:
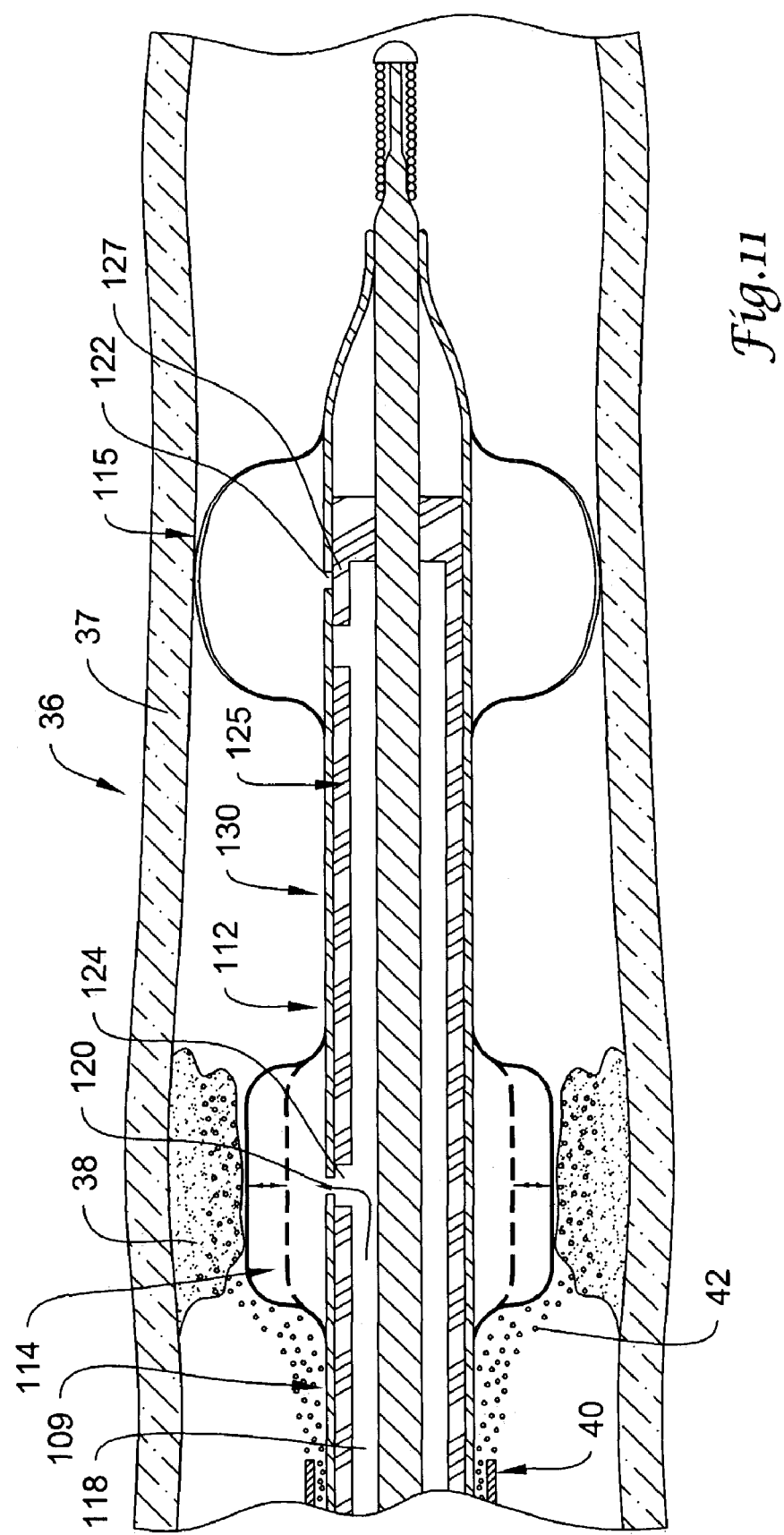
FIG. 11 is a partial cross-sectional view of the catheter and vessel of FIG. 10 showing a treatment material, such as a drug, is being released from a delivery device and the proximal balloon assembly being inflated and deflated proximate the treatment site to cause movement of the drug adjacent the treatment site.

Another example embodiment of such a catheter 130 is shown in FIGS. 10 and 11, wherein like reference numbers indicate similar structure. The catheter 130 includes a shaft assembly 112, a first deployable balloon assembly 114, and a second deployable balloon assembly 115, each connected proximate the distal end of shaft assembly 112 in a suitable manner, as discussed above. The shaft assembly 112 includes an outer tubular member 109 defining a lumen 118. In this embodiment, however, the outer tubular member 109 includes only two openings 120 and 122, which are disposed under and in fluid communication with the first and second balloon assemblies 114 and 115, respectively. Therefore, this embodiment does not include an opening in the outer tubular member 109 that may function as a treatment material release port.

The apparatus also includes a member 125 that is adapted to selectively block and/or allow fluid communication between the openings 120 and 122, and the lumen 118. In this embodiment, the member 125 includes two openings 124 and 127, each disposed in and extending through the wall of the member 125. Again, these openings can be selectively spaced along the length of the member 125 such that when the member 125 is positioned at a predetermined location within the lumen 118, one or more of the openings 124 or 127 can be selectively positioned adjacent to, and allow for fluid communication between the one or more of the openings 120 or 122 and the lumen 118. Additionally, the openings 124 or 127 can be selectively spaced along the length of the member 125 such that when the member is positioned at an alternative predetermined location within the lumen 118, the openings 124 or 127 can be selectively positioned away from one or more of the openings 120 or 122, and as a result, the wall of the member 125 blocks fluid communication between the openings 120 or 122 and the lumen 118.

FIG. 10 shows the catheter 130 disposed in a blood vessel 36 having a vessel wall 37 and a treatment site 38. The catheter 130 is disposed within the vessel 36 such that at least one of the balloon assemblies 114 or 115 is disposed adjacent the treatment site 38. In the embodiment shown, the more proximal balloon assembly 114 is disposed adjacent the treatment site 38, while the more distal balloon assembly 115 is disposed in a position distal to the treatment site 38. In FIG. 10, the movable inner member 125 is positioned within the lumen 118 such that the opening 126 is disposed adjacent to and in fluid communication with opening 122, and the more distal balloon assembly 115 is being inflated to engage the inner surface of the vessel wall 37.

Referring now to FIG. 11, the movable inner member 125 has been moved into a position within the lumen 118 such that the opening 122 is blocked by the inner member 125, but the opening 124 is disposed adjacent to and in fluid communication with opening 120. The balloon assembly 114 can then be inflated (deployed) and deflated (un-deployed) repeatedly adjacent the treatment site 38 to cause movement of the fluid. In this embodiment, a treatment material 42, such as a drug or medicine, can be released into the vessel through the guiding or infusion catheter 40, however, in other embodiments, other modes of introducing or releasing the treatment fluid into the vessel are contemplated. The repeated inflation (deployment) and deflation (un-deployment) of the balloon assembly 114 adjacent the treatment site 38 to cause movement of the fluid can create an interface between the treatment site and the treatment material, as discussed above with regard to the first embodiment. Also, as discussed above, the occlusion of the blood flow, for example, by the distal balloon assembly 115 can aid in maintaining the concentration of the treatment material 42 in the vessel 36 adjacent the treatment site 38.

Also as discussed above, it should be understood that in other embodiments, the more distal balloon assembly 115 may be positioned within the vessel such that it is disposed adjacent the treatment site 38, and can be used to create fluid movement while the more proximal balloon assembly 114 is disposed in a position proximal to the treatment site 38, and can be used to occlude the vessel. In such embodiments, the operation of the inner member 125 would essentially be reversed.

Figure 12:
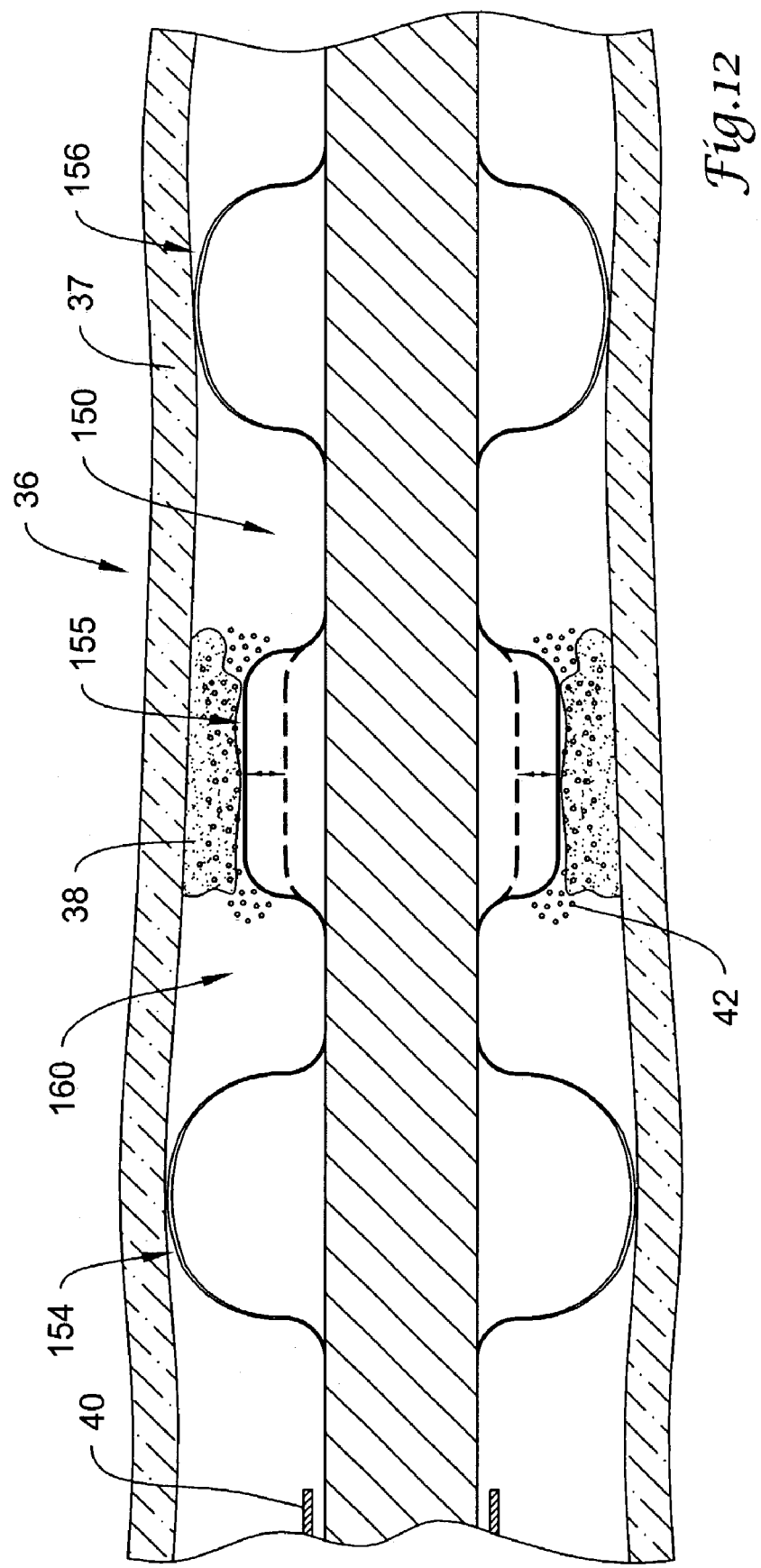
FIG. 12 is a partial side view of another example embodiment of balloon catheter having three balloon assemblies shown in cross section, wherein the catheter is disposed in a vessel proximate a treatment site, a treatment material has been released into the vessel, the distal and proximal balloon assemblies have been inflated, and the intermediate balloon assembly is being inflated and deflated proximate the treatment site to cause movement of the treatment material adjacent the treatment site.

FIG. 12 shows cross-sectional view of another alternative embodiment of an apparatus for use in treating intravascular disease, the apparatus including a balloon catheter 150. The catheter 150 may be similar in construction to those disclosed above, however, in this embodiment, the catheter 150 includes three deployable structures in the form of balloon assemblies 154, 155, and 156. The catheter 150 can have a fixed-wire design, or an over the wire design. Additionally, the catheter 150 can include one or more guidewire and/or inflation lumens disposed in a coaxial manner, or a side-by-side manner. Furthermore, in some embodiments, the catheter 150 may include an apparatus that is adapted and/or configured to selectively block and/or allow fluid communication between the balloon assemblies 154, 155, and 156, and one or more lumens, for example, structure such as the movable inner member 125 as discussed above with regard to FIGS. 7-11.

FIG. 12 shows the catheter 150 disposed in a blood vessel 36 having a vessel wall 37 and a treatment site 38. The catheter 150 can be introduced and navigated within the vessel using convention techniques. The catheter 150 is disposed within the vessel such that the balloon assembly 155 is disposed adjacent the treatment site 38, the balloon assembly 154 is disposed in a position proximal to the treatment site 38, and balloon assembly 156 is disposed in a position distal to the treatment site 38. The distal balloon assembly 156 can then be inflated to engage the inner surface of the vessel wall 37, and thereby occlude the flow of blood within the vessel. A treatment material 42, such as a drug or medicine, can be released into the vessel. In the embodiment shown, the treatment material 42 can be released into the vessel adjacent the treatment site through the guiding or infusion catheter 40. For example, the catheter 40 could be advanced over the deflated balloon assembly 154 such that it is adjacent the treatment site 38, and the treatment material could be introduced adjacent the treatment site 38. After, or during the release of the treatment material 42, the catheter can be withdrawn to a position proximal of the balloon assembly 154. However, in other embodiments, other modes of introducing or releasing the treatment material 42 into the vessel are contemplated. The proximal balloon assembly 154 can then also be inflated to engage the inner surface of the vessel wall 37, and thereby occlude the flow of blood within the vessel. As such, the inflation of the balloon assemblies 154 and 156 create an enclosed treatment area 160 disposed there between.

The occlusion of the blood flow by both the distal and proximal balloon assemblies 156 and 154 to create the enclosed treatment area 160 can further increase the concentration of the treatment material 42 in the vessel 36 adjacent the treatment site 38. The enclosed treatment area 160 will prevent dilution of the treatment material 42, and reduce the likelihood that the material will be carried away by the blood flowing in the vessel. As such, the concentration of the treatment material adjacent the treatment site can be maintained at relatively high levels, and the treatment material can be maintained adjacent the treatment site in higher concentration levels for longer periods of time. By increasing the concentration of the treatment materials adjacent the treatment site, the effectiveness of the treatment material upon the treatment site can be enhanced. In embodiments where the treatment site may include or be disposed within a branch vessel, the occlusion of the blood flow by both the distal and proximal balloon assemblies 156 and 154 may allow for additional control of the flow of the treatment materials into the branch vessel.

The intermediate balloon assembly 155 can then be inflated (deployed) and deflated (un-deployed) repeatedly adjacent the treatment site 38. The repeated inflation (deployment) and deflation (un-deployment) of the balloon assembly 155 adjacent the treatment site 38 to cause movement of the fluid can create an interface between the treatment site and the treatment material, as discussed above with regard to the first embodiment.

Figure 13:
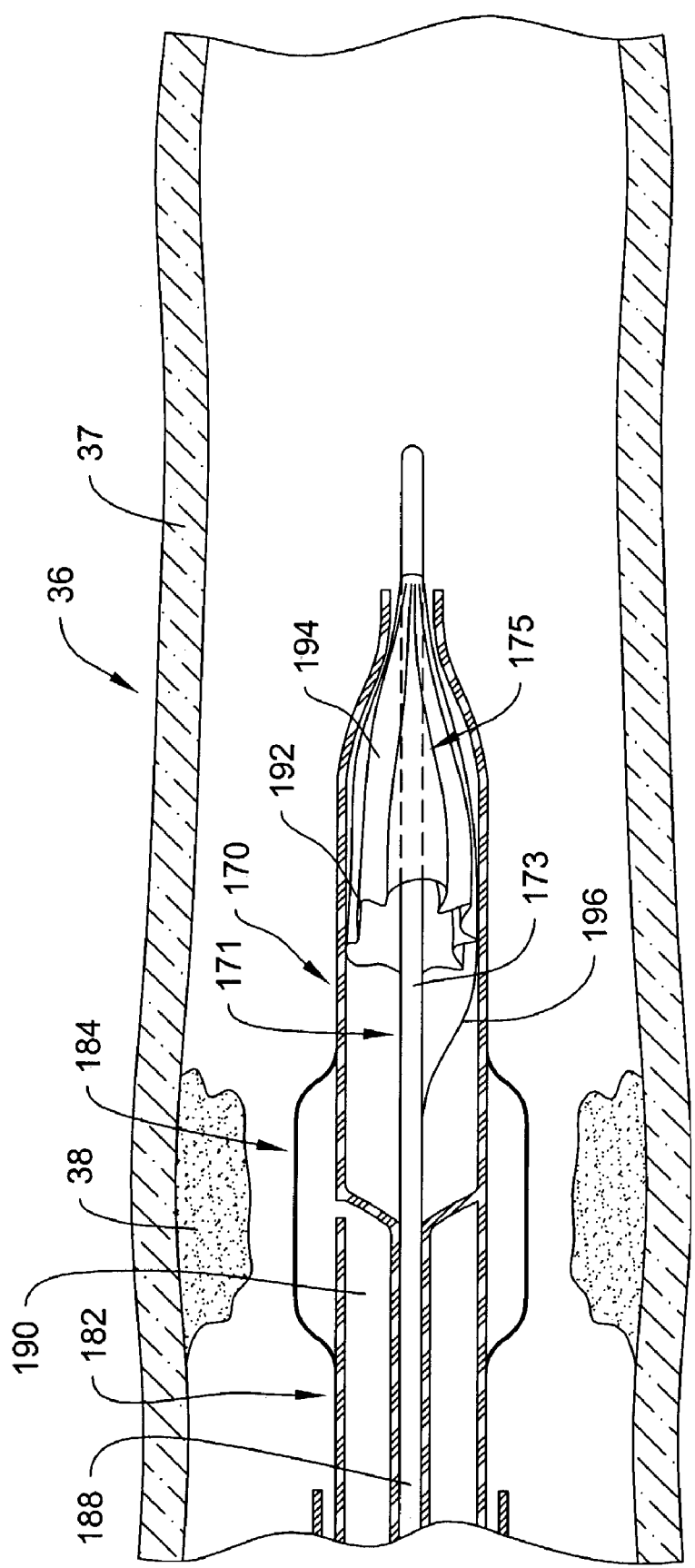
FIG. 13 is a partial cross-sectional view of another example embodiment of over-the-wire balloon catheter having a single balloon assembly disposed over a core member including a selectively deployable distal protection filter on the end thereof, wherein the catheter is disposed in a vessel proximate a treatment site.
Figure 14:
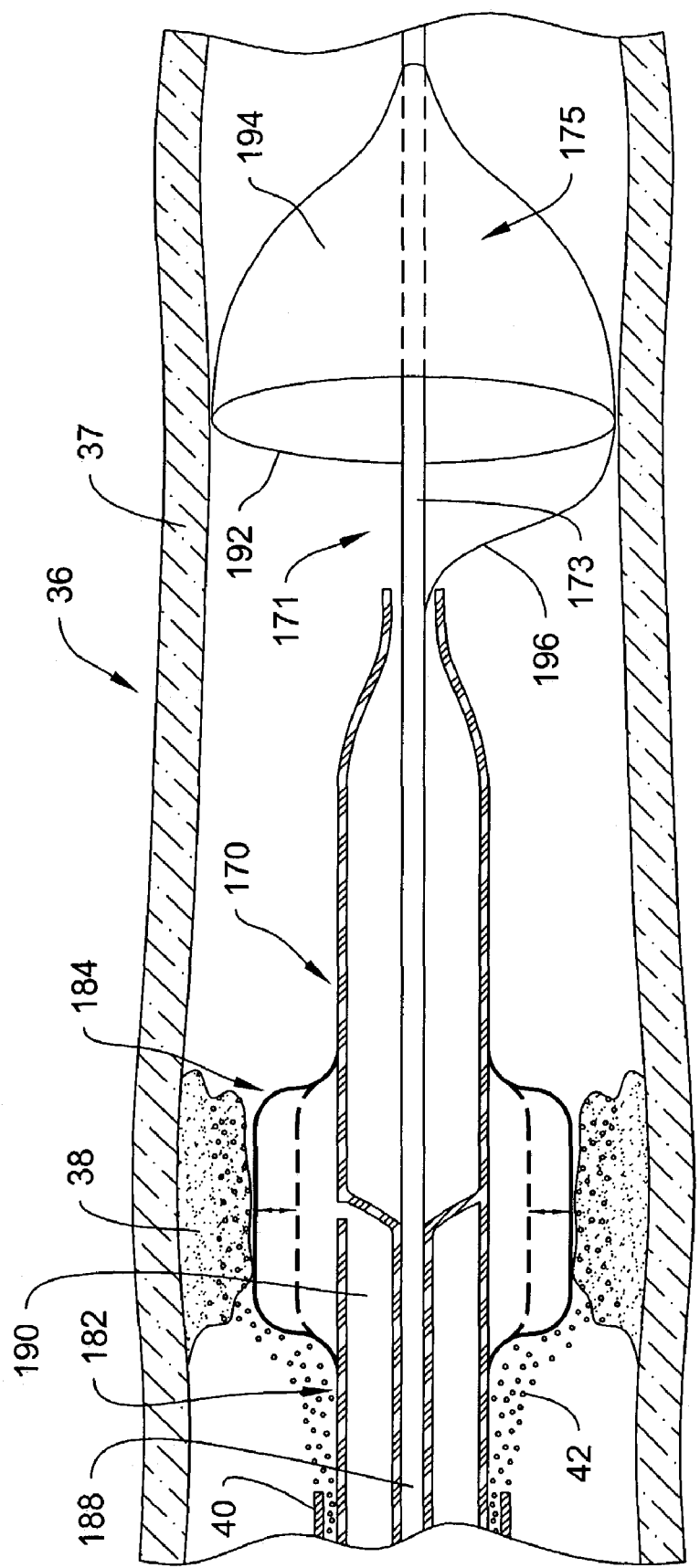
FIG. 14 is a partial cross-sectional view of the catheter, the core member, and the vessel of FIG. 13, showing the distal protection filter on the core member in a deployed state, a treatment material, such as a drug, being released from a delivery device, and the balloon assembly being inflated and deflated proximate the treatment site to cause movement of the drug adjacent the treatment site.

FIGS. 13-14 show another alternative embodiment of an apparatus, wherein an embolic protection device is used as one of the deployable structures. The apparatus includes an over-the-wire (OTW) balloon catheter 170 disposed over an embolic protection device 171 including a core wire 173 and a filter member 175 on the distal end thereof.

The balloon catheter 170 can include a shaft assembly 182, and a deployable balloon assembly 184 connected proximate the distal end of shaft assembly 182. The shaft assembly 182 may have conventional dimensions and may be made of conventional materials suitable for intravascular navigation as in, for example, conventional clot treatment, angioplasty or stent deployment procedures, or the like. The shaft assembly 182 includes a wire lumen 188 and an inflation lumen 190. In some embodiments, the wire lumen 188 may extend the entire length of the catheter shaft 182 (e.g. over-the-wire catheter), or it may extend along a portion of the catheter shaft 182, wherein it exits the catheter shaft 182 in the distal portion proximate the distal end (e.g. single operator exchange catheter). The inflation lumen 190 allows fluid communication between an inflation source and the deployable balloon assembly 184. The shaft assembly 182 may be a multiple lumen (i.e. side-by-side) design or a coaxial design as shown. In some embodiments, a manifold assembly (not shown) may be connected to the proximal end of the shaft assembly 182, for example, as discussed above in other embodiments.

The embolic protection device 171 is shown disposed within the wire lumen 188. The device 171 may include an elongate shaft or guidewire 173 having an embolic protection filter 175 coupled thereto. The core wire 173 may have conventional guidewire or distal protection device dimensions and may be made of conventional materials suitable for intravascular navigation as in, for example, conventional clot treatment, diagnostic, angioplasty, stent deployment, distal protection, or other such navigation and/or treatment procedures. The filter 175 may include a filter frame 192 and a filter material or fabric 194 coupled to filter frame 192. In general, the filter 175 may be adapted to operate between a first generally collapsed configuration and a second generally expanded configuration for collecting debris in a body lumen. In some embodiments, the frame 192 may include a "self-expanding" shape-memory material such as nickel-titanium alloy (to bias filter 175 to be in the second expanded configuration). Additionally, frame 192 may include a radiopaque material or include, for example, a radiopaque wire disposed about a portion thereof. Filter material 194 can be drilled (for example, formed by known laser techniques) or otherwise manufactured to include at least one opening. The holes or openings can be sized to allow blood flow there through but restrict flow of debris or emboli floating in the body lumen or cavity. One or more struts 196 may extend between frame 192 and shaft 173 and be coupled to shaft 173.

FIG. 13 shows the catheter 170 disposed in a blood vessel 36 having a vessel wall 37 and a treatment site 38. The embolic protection device 171 is shown disposed within the wire lumen 188 such that the filter member 175 is in a first generally collapsed configuration. The catheter 170 and embolic protection device 171 can be introduced and navigated within the vessel using convention techniques. The catheter 170 is disposed within the vessel such that the balloon assembly 184 is disposed adjacent the treatment site 38, and the distal end of the catheter is disposed in a position distal to the treatment site 38.

Referring now to FIG. 14, the embolic protection device 171 can be advanced distally within the wire lumen 188 such that the filter member 175 is positioned within the vessel distally of the catheter 170. The filter 175 is then deployed into the expanded configuration for collecting debris in a vessel. A treatment material 42, such as a drug or medicine, can be released into the vessel. In the embodiment shown, the treatment material 42 can be released into the vessel adjacent the treatment site through the guiding or infusion catheter 40, however, in other embodiments, other modes of introducing or releasing the treatment fluid into the vessel are contemplated. The balloon assembly 184 can be inflated (deployed) and deflated (un-deployed) repeatedly adjacent the treatment site 38. The repeated inflation (deployment) and deflation (un-deployment) of the balloon assembly 184 adjacent the treatment site 38 to cause movement of the fluid can create an interface between the treatment site 38 and the treatment material 42, as discussed above with regard to the first embodiment.

FIG. 15 shows another alternative embodiment, similar to that of FIGS. 13-14, wherein like reference numbers indicate similar structure. The apparatus includes an over-the-wire (OTW) balloon catheter 170 disposed over an embolic protection device 171 including a core wire 173 and a filter member 175 on the distal end thereof, as in the embodiment shown in FIGS. 13-14. However, in this embodiment, the balloon catheter 170 includes two deployable balloon assemblies 184 and 185 connected proximate the distal end of shaft assembly 182.

FIG. 15 shows the catheter 170 disposed in a blood vessel 36 having a vessel wall 37 and a treatment site 38. During insertion, the embolic protection device 171 can be disposed within the wire lumen 188 in a first generally collapsed configuration, for example, as shown in FIG. 13 in the embodiment above. Once the catheter 170 is disposed within the vessel such that the balloon assembly 184 is disposed adjacent the treatment site 38, the embolic protection device 171 can be advanced distally within the wire lumen 188 such that the filter member 175 is positioned within the vessel distally of the catheter 170, and the filter 175 is deployed into the expanded configuration, as shown. A treatment material 42, such as a drug or medicine, can be released into the vessel, for example, through a guiding or infusion catheter 40, however, in other embodiments, other modes of introducing or releasing the treatment fluid into the vessel are contemplated. The more proximal balloon assembly 185 can be inflated to occlude the blood vessel, and the more distal balloon assembly 184 can be inflated (deployed) and deflated (un-deployed) repeatedly adjacent the treatment site 38. As in the other embodiments discussed above, the repeated inflation (deployment) and deflation (un-deployment) of the balloon assembly 184 adjacent the treatment site 38 to cause movement of the fluid can create an interface between the treatment site and the treatment material. Additionally as discussed above, the occlusion of the blood flow, for example, by the balloon assembly 185 disposed at a location proximal to the treatment site can increase the concentration of the treatment material 42 in the vessel 36 adjacent the treatment site 38.

FIGS. 16-19 show another alternative embodiment of an apparatus for treating intravascular disease. FIG. 16 is a partial side view of the apparatus, which includes a catheter 210 including a shaft assembly 212 that includes an elongated tubular body 214 defining a lumen 218. The shaft assembly includes a distal portion 217 and a proximal portion (not shown). One or more apertures or openings are defined in the tubular body 214 in the distal portion of the shaft assembly 212. The embodiment shown includes two openings 220 and 222 are defined through the tubular body 214 and are in fluid communication with the lumen 218 and the exterior of the catheter 210.

The apparatus also includes a core wire 223 that is adapted to be disposed within the lumen 218, as seen in the cross sectional view of FIG. 17. The core wire 223 may have conventional guidewire dimensions and may be made of conventional materials and structure suitable for intravascular navigation as in, for example, conventional diagnostic, clot treatment, angioplasty, stent deployment, distal protection, or other such navigation and/or treatment procedures. The core wire 223 is adapted and/or configured such that it can move or slide longitudinally along the lumen 218 in the catheter 210. The core wire 223 includes one or more fluid moving members 225 connected thereto. In this embodiment, the fluid moving members include a plurality of flexible filaments or wires 225 attached to the core wire 223, however, in other embodiments the fluid moving members may include any of a broad range of structure that can be adapted to perform the desired task. The fluid moving members 225 can be adapted to include a first generally collapsed configuration when contained within the lumen 218 of the catheter 210, and a second, generally expanded configuration when the fluid moving members are not contained within the lumen 218. As such, the fluid moving members 225 are adapted and/or configured such that when the core wire 223 is appropriately positioned in a predetermined location along the length of the shaft assembly 212, at least some of the fluid moving members 225 can extend from the core wire 223 in the lumen 218 through the one or more openings 120 and 122 to a position outside of, or exterior to the catheter 210. The core wire 223 can be rotated and/or moved longitudinally relative to the catheter shaft 212 to create movement in the fluid moving members 225.

FIG. 18 shows the catheter 210 disposed in a blood vessel 36 having a vessel wall 37 and a treatment site 38. The catheter 210 can be introduced and navigated within the vessel using convention techniques. For example, a separate guidewire (not shown) may be introduced into the vessel and navigated to a position adjacent the treatment site 38, and the catheter 210 can then be advanced over the guidewire into a position adjacent the treatment site 38. Alternatively, a guide member, such as a guide or introducer catheter can be advanced to a position adjacent the treatment site, either alone or over a guidewire, and the catheter 210 could then be advanced within the guide catheter to a position adjacent the treatment site. In yet other embodiments, the catheter 210 could be navigated to the treatment site without the aid of another device, and may or may not include the core wire 223 disposed in the lumen 218 thereof.

As indicated, during insertion and navigation of the catheter 210, the core wire 223 may or may not be disposed in the lumen 218 of the catheter 210. If the core wire 223 is disposed in the lumen 218 during insertion or navigation to the treatment site, the core wire 223 can be positioned in the lumen such that fluid moving members 225 are spaced from the openings 220 and 222 and are in the first generally collapsed configuration within the lumen 218, for example, as shown in FIG. 18. In FIG. 18, the fluid moving members 225 are shown in a position proximal of the openings 220 and 222, however, in other embodiments, the fluid moving members may be in a position distal of the openings 220 and 222. In yet other embodiments, the core wire 223 may not be disposed in the lumen 218 of the catheter 210 during insertion and navigation of the catheter 210, and once the catheter is in position, the core wire 223 may be introduced into the lumen 218 of the catheter 210.

As shown in FIG. 18, the catheter 210 is disposed within the vessel such that the openings 220 and 222 are disposed adjacent the treatment site 38. The core wire 223 is positioned in the lumen 218 such that fluid moving members 225 are spaced from the openings 220 and 222 and are in a first generally collapsed configuration within the lumen 218.

Referring now to FIG. 19, the core wire 223 can be advanced within the lumen 218 such that one or more of the fluid moving members 225 are positioned within the openings 220 and 222, and extend from the first generally collapsed configuration to the second, expanded configuration. At least some of the fluid moving members 225 can extend from the core wire 223 through the one or more openings 120 and 122 to a position adjacent the treatment site 38, and in some embodiments, may make contact with a portion of the treatment site 38. In some embodiments, a treatment material 42, such as a drug or medicine, can be released into the vessel. In the embodiment shown, the treatment material 42 can be released into the vessel adjacent the treatment site through the openings 220 and 222 of the catheter 210, however, in other embodiments, other modes of introducing or releasing the treatment fluid into the vessel are contemplated. After, or during the release of the treatment material, the core wire 223 can be rotated and/or moved longitudinally relative to the catheter shaft 212, and the fluid moving members 225 cause movement of the fluid, and create an interface between the treatment site 38 and the treatment material 42, as discussed above with regard to the first embodiment.

In other embodiments, portions of the fluid moving members 225 may make contact with the treatment site 38, and the movement of the members 225 and/or the movement of the fluid adjacent the treatment site 38 may act to remove tissue or other material from the treatment site 38. For example, if the treatment site includes a blood clot, the movement of the members 225 and/or the movement of the fluid adjacent the treatment site may remove or break free portions of the blood clot.

Refer now to FIG. 20, which is a partial cross-sectional view of another example embodiment of an assembly for use in treatment of vascular disease similar to that shown in FIGS. 16-19, wherein like reference numbers indicate like structure. In this embodiment, however, the fluid moving members 225 include one or more looped filaments or wires connected to the core wire 223. As shown in FIG. 20, the apparatus can be used in an essentially similar manner to the embodiment described above with reference to FIGS. 16-19.

FIG. 21 is a partial cross-sectional view of another example embodiment of an assembly for use in treatment of vascular disease similar to that shown in FIGS. 16-20, wherein like reference numbers indicate like structure. In this embodiment, however, the fluid moving members 225 include one or more impeller or paddle members 225 connected to the core wire 223. The impeller or paddle members 225 can be shaped and sized appropriately to give the desired effect of fluid moving and/or tissue and/or other material removal from the treatment site 38. As shown in FIG. 21, the apparatus can be used in an essentially similar manner to the embodiment described above with reference to FIGS. 16-20.

With each of the embodiments described above with reference to FIGS. 16-21, it should be understood that any of a broad variety of structures may be used as the fluid moving structures or members 225, and that the embodiments shown are included only as example embodiments.

Refer now to FIGS. 22 and 23 which are partial cross-sectional views of another example embodiment of an apparatus for use in treatment of vascular disease similar to that shown in FIGS. 16-21, wherein like reference numbers indicate similar structure. FIG. 22 shows one cross sectional view of the apparatus, and FIG. 23 shows another cross sectional view when the apparatus is rotated ninety degrees about its longitudinal axis from the view shown in FIG. 22. In this embodiment, the catheter 230 is a balloon catheter including a balloon assembly 226 disposed thereon. In the embodiment shown, the balloon assembly 226 is disposed at a position distal of the openings 220 and 222 in the body 214 of the catheter shaft 212, however, in other embodiments, the balloon assembly 226 may be disposed in a position proximal of the openings 220 and 222. The catheter shaft 212 includes an inflation lumen 227 extending there through, and in fluid communication with the balloon assembly 226 (FIG. 23).

The embodiment shown in FIGS. 22 and 23 can be employed in a similar manner to at least some of the embodiments described above. For example, the catheter 230 is disposed within the vessel such that the openings 220 and 222 are disposed adjacent the treatment site 38, and the balloon assembly 226 is disposed in a position distal of the treatment site 38. The balloon assembly 226 can then be deployed (inflated) to occlude the flow of blood in the vessel. The core wire 223 can be advanced within the lumen 218 such that one or more of the fluid moving members 225 are positioned within the openings 220 and 222, and extend from the first generally collapsed configuration to the second, expanded configuration. At least some of the fluid moving members 225 can extend from the core wire 223 through the one or more openings 220 and 222 to a position adjacent the treatment site 38, and in some embodiments, may make contact with a portion of the treatment site 38.

In some embodiments, a treatment material 42, such as a drug or medicine, can be released into the vessel. In the embodiment shown, the treatment material 42 can be released into the vessel adjacent the treatment site through the openings 220 and 220 of the catheter 210, however, in other embodiments, other modes of introducing or releasing the treatment material into the vessel are contemplated. After, or during the release of the treatment material, the core wire 223 can be rotated and/or moved longitudinally relative to the catheter shaft 212, and the fluid moving members 225 cause movement of the fluid, and create an interface between the treatment site and the treatment material, as discussed above with regard to the first embodiment. Additionally, in some embodiments, portions of the fluid moving members 225 may make contact with the treatment site, and the movement of the members 225 and/or the movement of the fluid adjacent the treatment site may act to remove tissue or other material from the treatment site 38. Furthermore, as discussed above, the occlusion of the blood flow, for example, by the balloon assembly 226 disposed at a location distal to the treatment site can increase the concentration of the treatment material in the vessel adjacent the treatment site.

FIG. 24 is a partial cross-sectional view of another example embodiment of an assembly for use in treatment of vascular disease similar to that shown in FIGS. 22-23, wherein like reference numbers indicate similar structure. In this embodiment, the catheter 230 includes two balloon assemblies 226 and 227 disposed thereon, with one balloon assembly 226 disposed at a position distal of the openings 220 and 222 and the other balloon assembly 227 disposed at a position proximal of the openings 220 and 222. The catheter shaft 212 can include two inflation lumens (not shown) extending there through, one in fluid communication with each of the balloon assemblies 226 and 227.

The embodiment shown in FIG. 24 can also be employed in a similar manner to at least some of the embodiments described above. For example, the catheter 230 is disposed within the vessel such that the openings 220 and 222 are disposed adjacent the treatment site 38, the balloon assembly 226 is disposed in a position distal of the treatment site 38, and the balloon assembly 227 is disposed in a position proximal of the treatment site 38. The balloon assembly 226 can then be deployed (inflated) to occlude the flow of blood in the vessel. The balloon assembly 227 can also be deployed (inflated) to occlude the flow of blood in the vessel, and to create an enclosed treatment area 260 between the two balloon assemblies 226 and 227, for example, as discussed above with regard to the embodiment shown in FIG. 12.

The core wire 223 can be advanced within the lumen 218 such that one or more of the fluid moving members 225 are positioned within the openings 220 and 222, and extend from the first generally collapsed configuration to the second, expanded configuration. At least some of the fluid moving members 225 can extend from the core wire 223 through the one or more openings 120 and 122 to a position adjacent the treatment site 38, and in some embodiments, may make contact with a portion of the treatment site 38.

In some embodiments, a treatment material 42, such as a drug or medicine, can be released into the vessel. In the embodiment shown, the treatment material 42 can be released into the vessel adjacent the treatment site through the openings 220 and 222 of the catheter 210, however, in other embodiments, other modes of introducing or releasing the treatment material 42 into the vessel are contemplated. After, or during the release of the treatment material 42, the core wire 223 can be rotated and/or moved longitudinally relative to the catheter shaft 212, and the fluid moving members 225 cause movement of the fluid, and create an interface between the treatment site 38 and the treatment material 42, as discussed above with regard to the first embodiment. Additionally, in some embodiments, portions of the fluid moving members 225 may make contact with the treatment site 38, and the movement of the members 225 and/or the movement of the fluid adjacent the treatment site 38 may act to remove tissue or other material from the treatment site 38. Furthermore, as discussed above, the occlusion of the blood flow, for example, by the balloon assemblies 226 and 227 to create an enclosed treatment area at a location adjacent to the treatment site can aid in maintaining the concentration of the treatment material 42 in the vessel 36 adjacent the treatment site 38.

Figure 27:
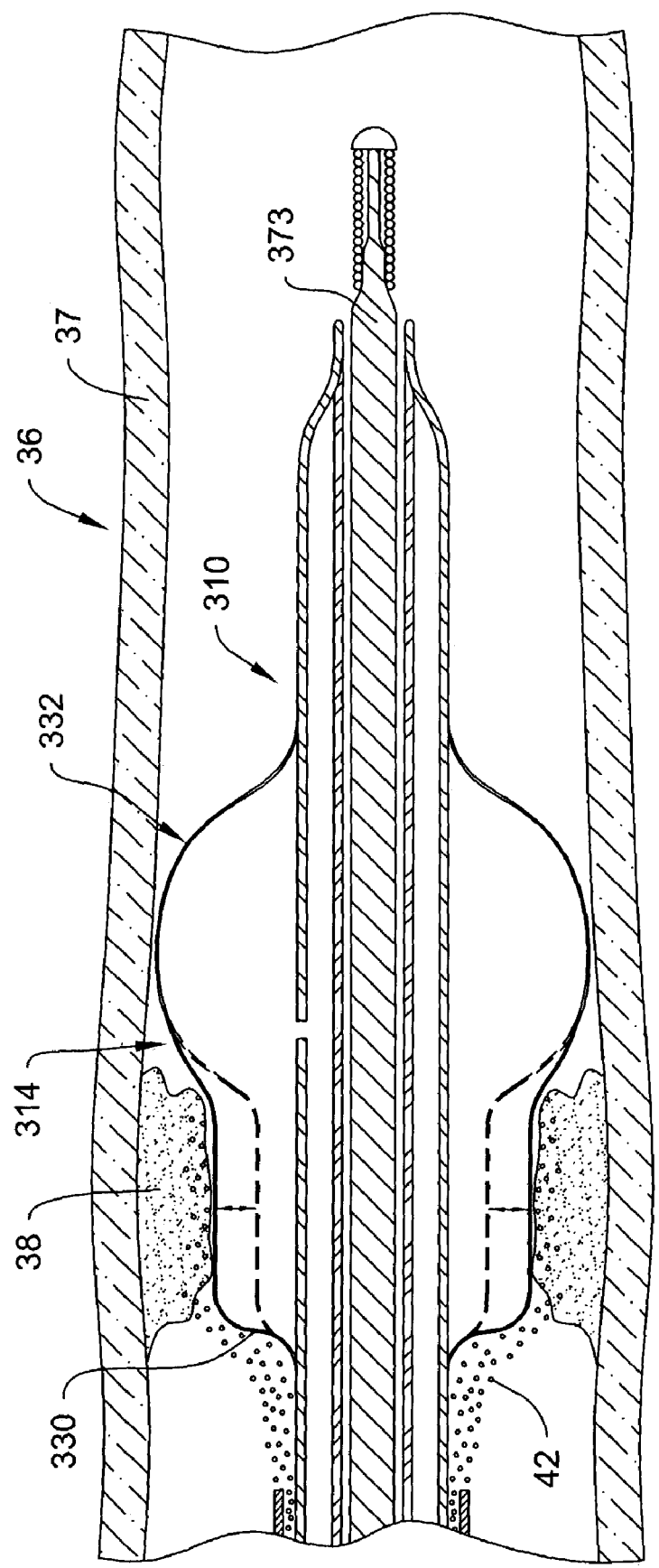
FIG. 27 is a partial cross-sectional view similar to that of FIG. 26, showing the proximal portion of the balloon member being inflated and deflated proximate the treatment site to cause movement of the drug adjacent the treatment site.

FIGS. 25-27 show partial cross-sectional views of another example embodiment of an assembly for use in treatment of vascular disease, the assembly including an over-the-wire balloon catheter 310 having a single balloon assembly 314 including a balloon member 328 that is adapted to have sections of varying inflation pressures along the length thereof. Although the catheter 310 is shown as an OTW catheter design, it should be understood that other catheter designs, for example, a Fixed-Wire (FW) design may be used without deviating from the spirit and scope of the invention.

The balloon catheter 310 includes a shaft assembly 312, including guidewire lumen 318 and an inflation lumen 319. In some embodiments, the guidewire lumen 318 may extend the entire length of the catheter shaft 312 (e.g. over-the-wire catheter), or it may extend along a portion of the catheter shaft 312, wherein it exits the catheter shaft 312 in the distal portion proximate the distal end (e.g. single operator exchange catheter). The inflation lumen 319 allows fluid communication between an inflation source and the deployable balloon assembly 314.

In the co-axial design shown, the shaft assembly 12 can include an inner tubular member 322, and an outer tubular member 326. The inner tubular member 322 defines the guidewire lumen 318, and the outer tubular member 326 is co-axially disposed about the inner tubular member 322 to define the inflation lumen 319 there between. In some embodiments, a manifold assembly (not shown) may be connected to the proximal end of the shaft assembly 312, as discussed above with regard to other embodiments.

The balloon assembly 314 is connected to the outer surface of the shaft assembly 312 using suitable attachment means It should be understood that the embodiment shown is a schematic representation of one example embodiment, and that a broad variety of alternative structures and arrangements can be used to create the shaft assembly 12 and deployable balloon assembly 314.

The deployable balloon assembly 314 includes an expandable balloon portion 328 including a proximal portion 330 and a distal portion 332. The proximal and distal portions 330 and 332 are adapted and/or configured to have different inflation pressures relative to one another. In this regard, when a first predetermined inflation pressure is supplied to the balloon assembly 314, one of the proximal or distal portions 330 and 332 will inflate, while the other of the proximal or distal portions 330 and 332 remains deflated. Additionally, when a second predetermined inflation pressure that is greater than the first predetermined inflation pressure is supplied to the balloon assembly 314, the one of the proximal or distal portions 330 and 332 will remain inflated, and the other of the proximal or distal portions 330 and 332 will also inflate. This varying degree of inflation pressure can be imparted to the balloon assembly 314, for example, by the use of different materials or structures in the two portions 330 and 332 of the expandable balloon portion 328. For example, one portion of the expandable balloon portion 328 can include a material having a lower modulus of elasticity as compared to the other portion. This can be achieved, for example, by using different materials, for example different polymers having different flexibility characteristics. Additionally and/or alternatively, the structure of one portion of the balloon may be different from the structure of the other portion. For example, the thickness of the material used to construct the balloon portion 328 may be varied along the length thereof to achieve the desired flexibility characteristics. Furthermore, different portions of the expandable balloon portion 328 may be treated and/or cross-linked differently. For example, one portion may be cross-linked, such as by radiation cross-linking techniques, while the other portion is not.

In the embodiment shown, the proximal portion 330 is adapted and/or configured to include an inflation pressure that is relatively greater than the inflation pressure of the distal portion 332. As such, when a first predetermined pressure is supplied to the balloon assembly 314, the distal portion 332 will inflate, but the proximal portion 330 will not. Additionally, when a second, greater predetermined inflation pressure is supplied to the balloon assembly, the distal portion 332 will remain inflated, and the proximal portion 330 will also inflate.

The apparatus shown in FIGS. 25-27 can be used in a somewhat similar manner to the other embodiments already described herein. For example, FIG. 26 shows the catheter 310 disposed in a blood vessel 36 having a vessel wall 37 and a treatment site 38. The catheter 310 can be introduced and navigated within the vessel using convention techniques, for example, over a guidewire 373. The catheter 310 is disposed within the vessel 36 such that the proximal portion 330 of the balloon assembly 314 is disposed adjacent the treatment site 38, and the distal portion 332 of the balloon assembly 314 is disposed in a position distal to the treatment site 38. The distal portion 332 of the balloon assembly 314 can then be inflated by applying a first predetermined pressure to the balloon assembly 314. The distal portion 332 can be inflated to engage the inner surface of the vessel wall 37, and thereby occlude the flow of blood within the vessel 36. A treatment material 42, such as a drug or medicine, can be released into the vessel. In the embodiment shown, the treatment material 42 can be released into the vessel adjacent the treatment site through the guiding or infusion catheter 40, however, other modes of delivering the treatment material 42 are contemplated.

Refer now to FIG. 27, which shows that the proximal portion 330 of the balloon assembly 314 can then be inflated (deployed) and deflated (un-deployed) repeatedly adjacent the treatment site 38 by supplying and removing a second predetermined inflation pressure, greater than the first inflation pressure, to the balloon assembly 314. The repeated inflation (deployment) and deflation (un-deployment) of the proximal portion 330 of the balloon assembly 314 adjacent the treatment site 38 to cause movement of the fluid can create an interface between the treatment site and the treatment material 42, as discussed above with regard to the first embodiment. Additionally, the occlusion of the blood flow by the distal portion 332 of the balloon assembly aid in maintaining the concentration of the treatment material 42 in the vessel 36 adjacent the treatment site 38, as discussed above in other embodiments.

It should also be understood that in other embodiments, the arrangement could be reversed, such that the proximal portion 330 is adapted and/or configured to include an inflation pressure that is relatively less than the inflation pressure of the distal portion 332. In such embodiments, the distal portion 332 can be positioned within the vessel such that it is disposed adjacent the treatment site 38, while the proximal portion 330 can be disposed in a position proximal to the treatment site 38. The proximal portion 330 could then be inflated to engage the inner surface of the vessel wall 37, and the distal portion 332 could be repeatedly inflated and deflated to create the movement.

Figure 28:
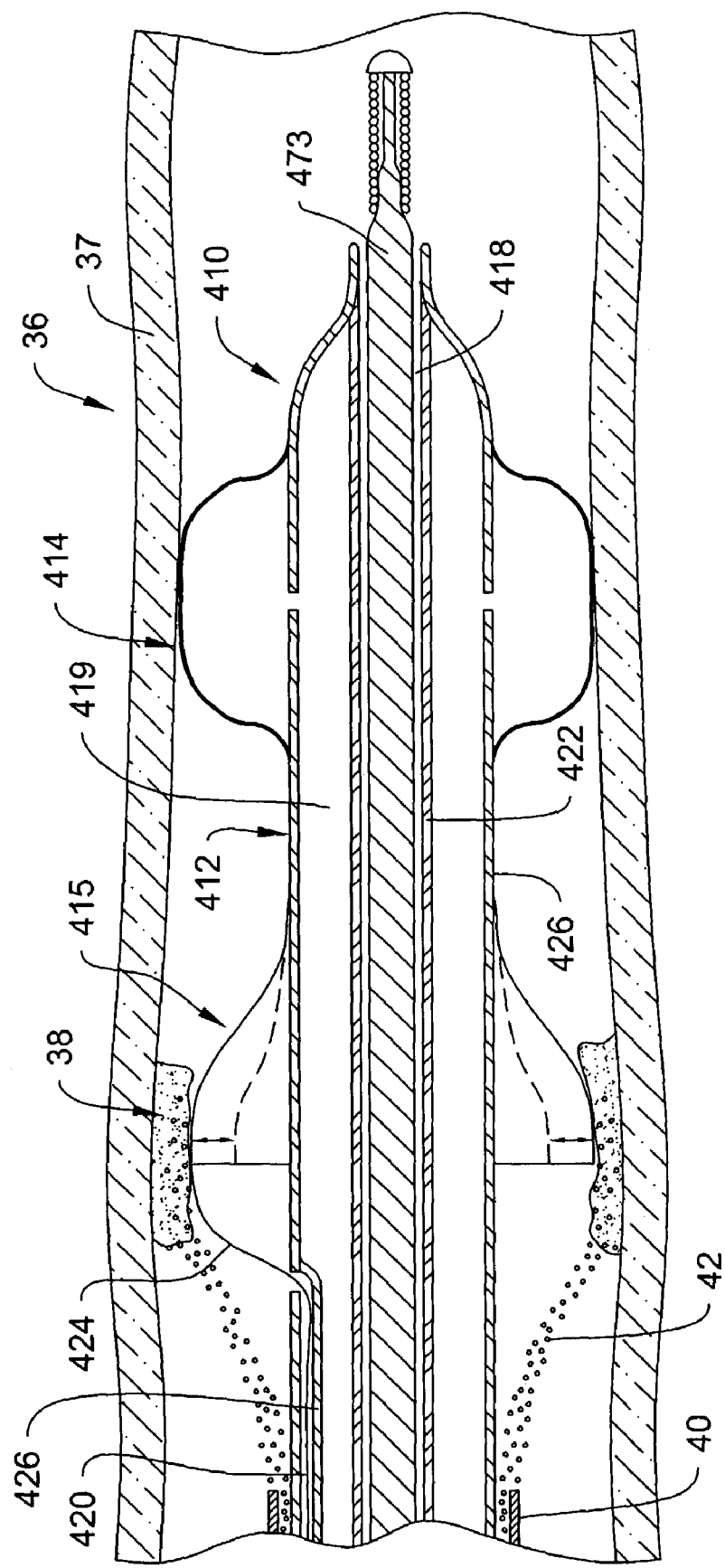
FIG. 28 is a partial cross-sectional view of another example embodiment of an assembly for use in treatment of vascular disease, the assembly including a balloon catheter having one distal balloon assembly, and including net or basket device, such as a distal protection filter, disposed on the catheter, wherein the catheter can be disposed in a vessel adjacent a treatment site, the distal balloon assembly can be inflated, a material, such as drugs, can be introduced into the vessel adjacent the treatment site, and the net or basket device can be deployed and un-deployed proximate the treatment site to cause movement of the drug adjacent the treatment site.

FIG. 28 is a partial cross-sectional view of another example embodiment of an assembly for use in treatment of vascular disease, the assembly including a balloon catheter 410 having a balloon assembly 414, and including a net or basket device 415, such as a distal protection filter, disposed on the catheter shaft 412. Although the catheter 410 is shown as an OTW catheter design, it should be understood that other catheter designs, for example, a Fixed-Wire (FW) design may be used without deviating from the spirit and scope of the invention.

The balloon catheter 410 includes a shaft assembly 412, including a guidewire lumen 418, an inflation lumen 419, and a device actuation lumen 420. In some embodiments, the guidewire lumen 418 may extend the entire length of the catheter shaft 412 (e.g. over-the-wire catheter), or it may extend along a portion of the catheter shaft 412, wherein it exits the catheter shaft 412 in the distal portion proximate the distal end (e.g. single operator exchange catheter). The inflation lumen 419 allows fluid communication between an inflation source and the deployable balloon assembly 414. The device actuation lumen 420 allows for communication from the proximal end of the catheter 410 to the net or basket device 415, for example, through the use of a pull cord 424, or other structure adapted and/or configured to engage the net or basket device 415.

The catheter 410 includes a modified co-axial design, wherein the shaft assembly 412 can include an inner tubular member 422, and an outer tubular member 426. The inner tubular member 422 defines the guidewire lumen 418, and the outer tubular member 426 is co-axially disposed about the inner tubular member 422 to define the inflation lumen 419 there between. Additionally, an additional tubular member 426 is disposed within the outer tubular member 426, and defines the device actuation lumen 420. In some embodiments, a manifold assembly (not shown) may be connected to the proximal end of the shaft assembly 412, as discussed above with regard to other embodiments.

The apparatus shown in FIG. 28 can be used in a somewhat similar manner to the other embodiments already described herein. For example, FIG. 28 shows the catheter 410 disposed in a blood vessel 36 having a vessel wall 37 and a treatment site 38. The catheter 410 can be introduced and navigated within the vessel using convention techniques, for example, over a guidewire 473. The catheter 410 is disposed within the vessel such that the net or basket device 415 is disposed adjacent the treatment site 38, and the balloon assembly 414 is disposed in a position distal to the treatment site 38. The balloon assembly 414 can then be inflated to engage the inner surface of the vessel wall 37, and thereby occlude the flow of blood within the vessel. A treatment material 42, such as a drug or medicine, can be released into the vessel. In the embodiment shown, the treatment material 42 can be released into the vessel adjacent the treatment site through the guiding or infusion catheter 40, however, other modes of delivering the treatment material 42, for example, through the lumen 420, are contemplated. The net or basket device 415 can then be repeatedly deployed and un-deployed, or otherwise moved within the vessel to cause movement of the fluid and create an interface between the treatment site 38 and the treatment material 42, as discussed above with regard to other embodiments. The deployment/un-deployment of the net or basket device 415 can be achieved, for example, by manipulation of the pull cord 424, or other structure adapted and/or configured to engage the device 415. Additionally, the occlusion of the blood flow by the balloon assembly 414 can aid in maintaining the concentration of the treatment material 42 in the vessel 36 adjacent the treatment site 38, as discussed above in other embodiments.

Figure 29:
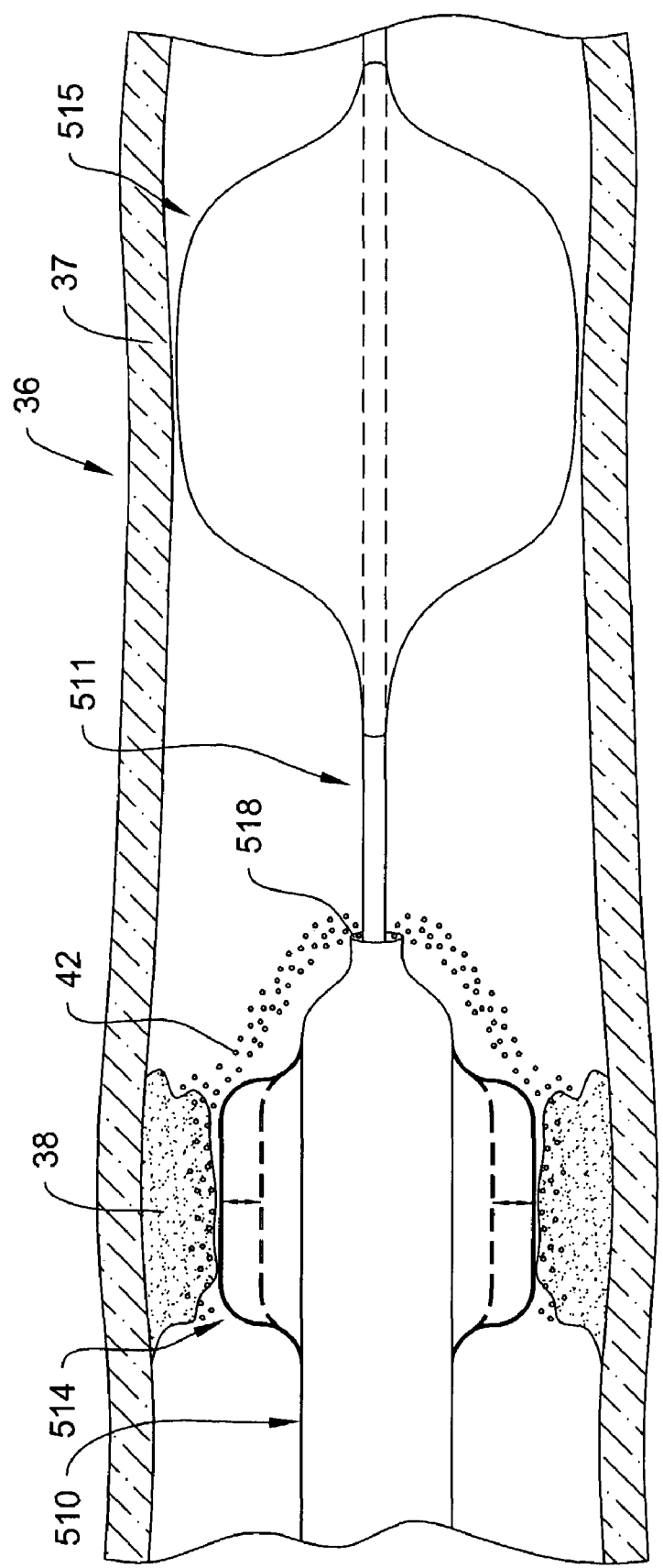
FIG. 29 is a partial cross-sectional view of another example embodiment of an assembly for use in treatment of vascular disease, the assembly including a first balloon catheter having a balloon assembly, and a second, balloon catheter having a balloon assembly extending from within an inner lumen of the first catheter assembly, wherein the first balloon assembly can be disposed in a vessel adjacent a treatment site, the second balloon assembly can be inflated in a position distal of the treatment site, and a treatment material, such as a drug, can be introduced into the vessel adjacent the treatment site, and the first balloon assembly can be deployed and un-deployed proximate the treatment site to cause movement of the drug adjacent the treatment site.

FIG. 29 is a partial cross-sectional view of another example embodiment of an assembly for use in treatment of vascular disease, the assembly including a first balloon catheter 510 having a balloon assembly 514, and a second balloon catheter 511 having a balloon assembly 515. The catheter 510 generally has an over the wire design including a central lumen 518. The catheter 511 can be either a OTW or a FW design. Either or both catheters 510 and 511 can include one or more lumens disposed in a coaxial manner, or a side-by-side manner. Furthermore, in some embodiments, either of both catheters 510 and 511 can include an apparatus that is adapted and/or configured to selectively block and/or allow fluid communication between the balloon assemblies 514 or 515, and one or more lumens, for example, structure such as the movable inner member 125 as discussed above with regard to FIGS. 7-11.

The apparatus shown in FIG. 29 can be used in a somewhat similar manner to the other embodiments already described herein. For example, FIG. 29 shows the catheter 510 disposed in a blood vessel 36 having a vessel wall 37 and a treatment site 38. The catheter 510 can be introduced and navigated within the vessel using convention techniques. The catheter 510 is disposed within the vessel such that the balloon assembly 514 is disposed in a position adjacent to the treatment site 38. The catheter 511 can be advanced through the lumen 518 of the catheter 510, and positioned within the vessel such that the balloon assembly 515 is disposed at a location distal of the treatment site 38. The balloon assembly 515 can then be inflated to engage the inner surface of the vessel wall 37, and thereby occlude the flow of blood within the vessel. A treatment material 42, such as a drug or medicine, can be released into the vessel. In the embodiment shown, the treatment material 42 can be released into the vessel adjacent the treatment site through the central lumen 518 of the catheter 510, however, other modes of delivering the treatment material 42, are contemplated. The balloon assembly 514 can then be repeatedly deployed and un-deployed, or otherwise moved within the vessel to cause movement of the fluid. The movement can create an interface between the treatment site 38 and the treatment material 42, as discussed above with regard to other embodiments. Additionally, the occlusion of the blood flow by the balloon assembly 515 can aid in maintaining the concentration of the treatment material 42 in the vessel 36 adjacent the treatment site 38, as discussed above in other embodiments.

Also as discussed above, it should be understood that in other embodiments, the more distal balloon assembly 515 may be positioned within the vessel such that it is disposed adjacent the treatment site 38, while the more proximal balloon assembly 514 is disposed in a position proximal to the treatment site 38. In such embodiments, the more proximal balloon assembly 514 could be used to occlude the vessel, while the more distal balloon assembly 515 could be used to create fluid movement.

It should be understood that this disclosure is, in many respects, only illustrative. Changes may be made in details, particularly in matters of shape, size, and arrangement of steps without exceeding the scope of the invention. For example, in many of the embodiments shown, a different type of deployable member may be used in place of the ones shown. For example, in some embodiments, a deployable filter member, or net or basket device may be used instead of the balloon assembly shown, and vice versa. Similarly, alternative deployable structure other than those particularly shown and described herein can be used to create motion and/or agitation within the vessel. Additionally, more or fewer deployable structures than those shown can be used on a variety of devices. Additionally, alternative catheter constructions or other such structure may be used. The invention's scope is, of course, defined in the language in which the appended claims are expressed.

What is claimed is:

1. A method of treating a treatment site in a blood vessel, the method comprising:
   providing an apparatus including, a first deployable structure and a second deployable structure;
   inserting the apparatus into the vessel adjacent the treatment site such that the first deployable structure is disposed adjacent the treatment site, and the second deployable structure is disposed at a location proximal or distal to the treatment site;
   introducing a treatment material into the vessel proximate the treatment site;
   deploying the second deployable structure within the vessel at the location proximal or distal the treatment site; and
   deploying the first deployable structure adjacent the treatment site to create movement of the treatment material adjacent the treatment site.

2. The method of claim 1, further including repeatedly deploying and un-deploying the first deployable structure adjacent the treatment site to create movement of the treatment material adjacent the treatment site.

3. The method of claim 1, wherein the first and second deployable structures each individually comprise a balloon assembly, net assembly, basket assembly, filament assembly, paddle assembly, impeller assembly, or filter assembly.

4. The method of claim 1, wherein the first and second deployable structures each individually comprise a balloon assembly, or filter assembly.

5. The method of claim 1, wherein the treatment material comprises a blood clot dissolving drug.

6. The method of claim 1, wherein the treatment material comprises TpA, urokinase, streptokinase, reteplase, or anistreplase.

7. The method of claim 1, wherein the vessel is a cranial blood vessel, and the treatment site includes a blood clot, and wherein the inserting step includes inserting the apparatus into the cranial vessel and the introducing step includes introducing a blood clot dissolving drug.

8. The method of claim 1, wherein the apparatus comprises a balloon catheter having tubular body, and the first and second deployable structures are inflatable balloon assemblies mounted on the tubular body.

9. The method of claim 1, wherein the first deployable structure comprises an inflatable balloon assembly and the second deployable structure comprises a filter assembly.

10. The method of claim 1, wherein the first deployable structure comprises a filter assembly and the second deployable structure comprises an inflatable balloon assembly.

11. The method of claim 1, wherein the apparatus comprises a balloon catheter including an elongated tubular body defining at least one lumen therein and a balloon assembly mounted thereon, the apparatus further comprising an elongated core member including a distal portion having a filter assembly mounted thereon, the core member being slidably disposed within the lumen of the catheter, and wherein the balloon assembly comprises the first deployable structure and the filter assembly comprises the second deployable structure.

12. The method of claim 11, wherein the elongated tubular body of the catheter includes a distal end, and during the insertion of the apparatus into the vessel, the filter assembly is disposed within the lumen of the catheter proximal of the distal end, and to deploy the filter assembly within the vessel, the filter assembly is advanced distally beyond the distal end of the tubular body of the catheter.

13. The method of claim 1, wherein the second deployable structure is deployed at a location proximal to the treatment site.

14. The method of claim 1, wherein the second deployable structure is deployed at a location distal to the treatment site.

15. The method of claim 1, wherein the apparatus further includes a third deployable structure, and wherein inserting the apparatus into the vessel includes disposing the first deployable structure adjacent the treatment site, disposing the second deployable structure at a location proximal to the treatment site, and disposing the third deployable structure at a location distal to the treatment site, and the method further includes deploying the third deployable structure within the vessel.

16. The method of claim 15, wherein the first, second, and third deployable structures each individually comprise a balloon assembly, a net assembly, a basket assembly, a filament assembly, a paddle assembly, an impeller assembly, or a filter assembly.

17. The method of claim 15, wherein the apparatus comprises a balloon catheter, and the first and second deployable structures each comprise an inflatable balloon assembly, and the third deployable structure comprises a filter assembly.

18. The method of claim 15 wherein the apparatus comprises a balloon catheter having an inner lumen, and the first and second deployable members comprise deployable balloon assemblies, the apparatus further including a distal protection device including a distal filter member, and wherein the distal filter member comprises the third deployable structure.

19. The method of claim 15, wherein the apparatus is a balloon catheter, and the second deployable structures comprises an inflatable balloon assembly, and the third deployable structure comprises a filter assembly.

20. The method of claim 1, wherein the apparatus further includes a delivery catheter, and the treatment material is introduced into the vessel through the delivery catheter.

21. An apparatus for treating a treatment site in a blood vessel, the apparatus comprising:
   an elongated tubular member including a distal portion;
   a structure for introducing treatment material to the treatment site;
   an first deployable structure connected to the distal portion of the tubular member, the first deployable structure adapted to be deployed and engage the blood vessel at a position proximal or distal of the treatment site; and a second deployable structure connected to the distal portion of the tubular member, the second deployable structure adapted to be deployed adjacent the treatment site to create movement of the treatment material adjacent the treatment site.

22. The apparatus of claim 21, wherein the first and second deployable structures are each individually selected from a balloon assembly, net assembly, basket assembly, filament assembly, paddle assembly, impeller assembly, or filter assembly.

23. The apparatus of claim 21, wherein the first and second deployable structures are each individually selected from a balloon assembly, or a filter assembly.

24. The apparatus of claim 21, wherein the elongated tubular member is adapted to extend within a cranial vessel, and the first and second deployable structures are adapted to be deployed in the cranial vessel.

25. The apparatus of claim 21, wherein the apparatus comprises a balloon catheter having tubular body, and the first and second deployable structures are inflatable balloon assemblies mounted on the tubular body.

26. The apparatus of claim 25, wherein the balloon catheter comprises one of an over-the-wire or a fixed wire balloon catheter.

27. The apparatus of claim 25, wherein the body of the balloon catheter comprises a plurality of lumens disposed in a coaxial arrangement.

28. The apparatus of claim 25, wherein the body of the balloon catheter comprises a plurality of lumens disposed in a side-by-side arrangement.

29. The apparatus of claim 21, wherein the second deployable structure is adapted to be repeatedly deployed and undeployed adjacent the treatment site.

30. The apparatus of claim 21, wherein the first deployable structure comprises an inflatable balloon assembly and the second deployable structure comprises a filter assembly.

31. The apparatus of claim 21, wherein the first deployable structure comprises a filter assembly and the second deployable structure comprises an inflatable balloon assembly.

32. The apparatus of claim 21, wherein the apparatus comprises a balloon catheter including an elongated tubular body defining at least one lumen therein and a balloon assembly mounted thereon, the apparatus further comprising an elongated core member including a distal portion having a filter assembly mounted thereon, the core member being slidably disposed within the lumen of the catheter, wherein the balloon assembly comprises the first deployable structure and the filter assembly comprises the second deployable structure.

33. The apparatus of claim 32, wherein the elongated tubular body of the catheter includes a distal end, the filter assembly is adapted to in a first, non-expanded configuration when disposed within the lumen of the catheter proximal of the distal end during the insertion of the apparatus into the vessel, the filter assembly further adapted to deploy to a second, expanded configuration when it is advanced distally beyond the distal end of the tubular body of the catheter within the vessel.

34. The apparatus of claim 21, wherein the first deployable structure is adapted to be deployed in a position within the vessel proximal of the treatment site.

35. The apparatus of claim 21, wherein the first deployable structure is adapted to be deployed in a position within the vessel distal of the treatment site.

36. The apparatus of claim 21, wherein the apparatus further includes a third deployable structure, and the first deployable structure is adapted to be deployed at a location proximal to the treatment site, and the third deployable structure is adapted to be deployed at a location distal to the treatment site.

37. The apparatus of claim 36, wherein the first, second, and third deployable structures are each individually selected from a balloon assembly, a net assembly, a basket assembly, a filament assembly, a paddle assembly, an impeller assembly, or a filter assembly.

38. The apparatus of claim 36, wherein the apparatus is a balloon catheter, and the first, second, and third deployable structures each comprise an inflatable balloon assembly.

39. The apparatus of claim 36, wherein the apparatus is a balloon catheter, and the first and second deployable structures each comprise an inflatable balloon assembly, and the third deployable structure comprises a filter assembly.

40. The apparatus of claim 36, wherein the apparatus is a balloon catheter, and the second deployable structures comprises an inflatable balloon assembly, and the third deployable structure comprises a filter assembly.

41. The apparatus of claim 21, wherein the apparatus further includes a delivery catheter.

\* \* \* \* \*

UNITED STATES PATENT AND TRADEMARK OFFICE
CERTIFICATE OF CORRECTION

| | |
|---|---|
| PATENT NO. | : 7,662,143 B2 |
| APPLICATION NO. | : 10/629114 |
| DATED | : February 16, 2010 |
| INVENTOR(S) | : Carrison et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 687 days.

Signed and Sealed this

Thirtieth Day of November, 2010

David J. Kappos
*Director of the United States Patent and Trademark Office*